US012311593B2

(12) United States Patent
Cordero et al.

(10) Patent No.: US 12,311,593 B2
(45) Date of Patent: May 27, 2025

(54) MELANIN BASED BIO-COMPOSITES FOR 3D PRINTING

(71) Applicant: THE JOHNS HOPKINS UNIVERSITY, Baltimore, MD (US)

(72) Inventors: Radames J. B. Cordero, Baltimore, MD (US); Arturo Casadevall, Baltimore, MD (US); Quigly Dragotakes, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 296 days.

(21) Appl. No.: 17/415,689

(22) PCT Filed: Dec. 20, 2019

(86) PCT No.: PCT/US2019/068043
§ 371 (c)(1),
(2) Date: Jun. 17, 2021

(87) PCT Pub. No.: WO2020/132559
PCT Pub. Date: Jun. 25, 2020

(65) Prior Publication Data
US 2022/0072763 A1 Mar. 10, 2022

Related U.S. Application Data

(60) Provisional application No. 62/898,948, filed on Sep. 11, 2019, provisional application No. 62/898,926, (Continued)

(51) Int. Cl.
*B29C 64/118* (2017.01)
*B29C 64/314* (2017.01)
(Continued)

(52) U.S. Cl.
CPC .......... *B29C 64/118* (2017.08); *B29C 64/314* (2017.08); *B33Y 10/00* (2014.12);
(Continued)

(58) Field of Classification Search
CPC ..... B29C 64/118; B29C 64/314; B29C 48/05; B29C 48/022; B29C 48/92; B33Y 10/00;
(Continued)

(56) References Cited

U.S. PATENT DOCUMENTS 5,047,447 A 9/1991 Gallas
5,380,359 A 1/1995 Honda et al.
(Continued)

FOREIGN PATENT DOCUMENTS

CN 103320332 9/2013
CN 107298838 A 10/2017
(Continued)

OTHER PUBLICATIONS

International Search Report and Written Opinion for PCT/US19/68043. Mailed Mar. 24, 2020. 9 pages.
(Continued)

*Primary Examiner* — Nahida Sultana
(74) *Attorney, Agent, or Firm* — Lisa Mueller; Casimir Jones S.C.

(57) ABSTRACT

Described are biocomposites comprising melanin. Uses of melanin biocomposites in methods of heat generation and radiation protection are also described. 3D printed filaments comprising melanin and methods and making and using thereof are further described.

7 Claims, 19 Drawing Sheets

Related U.S. Application Data filed on Sep. 11, 2019, provisional application No. 62/783,591, filed on Dec. 21, 2018.

(51) Int. Cl.
  *B33Y 10/00* (2015.01)
  *B33Y 70/10* (2020.01)
  *B33Y 80/00* (2015.01)
  *C08G 61/12* (2006.01)
  *C08L 67/02* (2006.01)

(52) U.S. Cl.
  CPC ............... *B33Y 70/10* (2020.01); *B33Y 80/00* (2014.12); *C08G 61/124* (2013.01); *C08L 67/02* (2013.01)

(58) Field of Classification Search
  CPC ...... B33Y 70/10; B33Y 80/00; C08G 61/124; C08L 67/02; B32B 27/10; B32B 27/40; C08K 5/3417; C09B 61/00; C12P 17/165; F24S 70/14
  See application file for complete search history.

(56) References Cited

U.S. PATENT DOCUMENTS

| | | | |
|---|---|---|---|
| 5,538,752 | A | 7/1996 | Blanchette et al. |
| 7,354,150 | B2 | 4/2008 | Sugimura et al. |
| 8,586,090 | B2 | 11/2013 | Dadachova et al. |
| 9,450,043 | B2 | 9/2016 | Nuzzo et al. |
| 9,523,160 | B2 | 12/2016 | Kim et al. |
| 2005/0156496 | A1* | 7/2005 | Takashima ......... C09K 11/7739 313/237 |
| 2007/0237829 | A1 | 10/2007 | Dadachova et al. |
| 2010/0123105 | A1* | 5/2010 | Gallas ...................... G02C 7/04 252/586 |
| 2011/0281070 | A1* | 11/2011 | Mittal .................... B05D 1/005 428/221 |
| 2012/0132930 | A1* | 5/2012 | Young .................. H05K 1/0313 257/E31.127 |
| 2013/0056244 | A1* | 3/2013 | Srinivas ............... H05K 1/0298 174/250 |
| 2014/0037674 | A1 | 2/2014 | Dadachova et al. |
| 2014/0257109 | A1 | 9/2014 | Nishikubo |
| 2016/0066601 | A1 | 3/2016 | Herr et al. |
| 2017/0066188 | A1 | 3/2017 | Luo et al. |
| 2018/0112040 | A1 | 4/2018 | Zhou et al. |
| 2019/0250431 | A1* | 8/2019 | Shan ..................... G02B 5/3075 |
| 2019/0297880 | A1 | 10/2019 | Shanmuganathan et al. |

FOREIGN PATENT DOCUMENTS

| | | |
|---|---|---|
| EP | 3228192 | 10/2017 |
| RU | 2565178 | 10/2015 |
| WO | WO 2017/212500 | 12/2017 |
| WO | WO 2020/132555 | 6/2020 |

OTHER PUBLICATIONS

Cao et al., Selenomelanin: An Abiotic Selenium Analogue of Pheomelanin. J Am Chem Soc. Jul. 22, 2020;142(29):12802-12810.
Lopusiewicz et al., New Poly(lactic acid) Active Packaging Composite Films Incorporated with Fungal Melanin., Polymers., 2018, vol. 10(4):386. 22 pages.
Malo et al., Morphological changes in melanized and non-melanized Cryptococcus neoformans cells post exposure to sparsely and densely ionizing radiation demonstrate protective effect of melanin. Fungal Biol. Jun. 2018;122(6):449-456.
MatterHackers. How to succeed when 3d printing with hylon. MatterHackers. www.matterhackers.com/articles/printing-with-nylon . 2014. Retrieved from the internet Feb. 25, 2020. 2 pages.
Nambier et al., Polymer-composite materials for radiation protection. ACS Appl Mater Interfaces. Nov. 2012;4(11):5717-26.
Nasa Science, Plastic Spaceships | Science Mission Directorate [Online]. P.L.B. 2005. Available at: https://science.nasa.gov/science-news/science-at-nasa/2005/25aug_plasticspaceships [Accessed: Mar. 13, 2017]. Printed May 16, 2022. 10 pages.
Ngo et al., Additive manufacturing (3D printing): A review of materials, methods, applications and challenges., Composites Part B: Engineering., 2018, vol. 143. pp. 172-196.
Ou-Yang et al., Spectral responses of melanin to ultraviolet A irradiation. J Invest Dermatol. Feb. 2004;122(2):492-6.
Shin et al., Melanin Nanoparticle-Incorporated Silk Fibroin Hydrogels for the Enhancement of Printing Resolution in 3D-Projection Stereolithography of Poly(ethylene glycol)-Tetraacrylate Bio-ink. ACS Appl Mater Interfaces. Jul. 18, 2018;10(28):23573-23582.
Shunk et al., A self-replicating radiation shield for human deep space exploration: radiotrophic fungi can attenuate ionizing radiation aboard the international space station. bioRxiv. 2020. 16 pages.
Viskadourakis et al., Electromagnetic shielding effectiveness of 3D printed polymer composites., Applied Physics A Solids and Surfaces., 2017, vol. 123(12):736. 7 pages.
Wang et al., Mechanical properties of thermoplastic elastomers of poly(butylene terephthalate) and poly(ethylene glycol) in a bending deformation., Journal of Applied Polymer Science., 1994, vol. 51. pp. 145-151.
European Patent Office, Extended European Search Report for EP Application No. 19898875.0, dated Jan. 26, 2023. 13 pages.
International Search Report and Written Opinion for PCT/US19/68034. Mailed Apr. 27, 2020. 11 pages.
Albuquerque et al., Quorum sensing-mediated, cell density-dependent regulation of growth and virulence in Cryptococcus neoformans., MBio., (2013), vol. 5(1):e00986-00913. 15 pages.
Al-Doory., The ultrastructure of Cryptococcus neoformans., Sabouraudia: Journal of Medical and Veterinary Mycology., (1971), pp. 115-118, vol. 9(2).
Almagro Armenteros et al., SignalP 5.0 improves signal peptide predictions using deep neural networks., Nature Biotechnology., (2019), pp. 420-423, vol. 37.
Alviano et al., Characterization of Fonsecaea pedrosoi melanin., Journal of Genetic Microbiology., (1991), pp. 837-844, vol. 137.
Baker et al., Chitinases are essential for sexual development but not vegetative growth in Cryptococcus neoformans. Eukaryot Cell., (2009), pp. 1692-1705, vol. 8(11).
Baker et al., Chitosan, the deacetylated form of chitin, is necessary for cell wall integrity in Cryptococcus neoformans., Eukaryotic Cell., (2007), pp. 855-867, vol. 6(5).
Banks et al., A chitin synthase and its regulator protein are critical for chitosan production and growth of the fungal pathogen Cryptococcus neoformans., Eukaryotic Cell., (2005), pp. 1902-1912, vol. 4(11).
Bissig et al., PMEL Amyloid Fibril Formation: The Bright Steps of Pigmentation., International Journal of Molecular Sciences., (2016), vol. 17(9):1438. 14 pages.
Brach et al., Reassessment of the role of plasma membrane domains in the regulation of vesicular traffic in yeast., Journal of Cell Science., (2011), pp. 328-337, vol. 124(3).
Bull., Chemical composition of wild-type and mutant Aspergillus nidulans cell walls. The nature of polysaccharide and melanin constituents., Journal of Genetic Microbiology., (1970), pp. 75-94, vol. 63.
Bungeler et al., Insight into the Final Step of the Supramolecular Buildup of Eumelanin., Langmuir., (2017), pp. 6895-6901, vol. 33.
Bungeler et al., The Supramolecular Buildup of Eumelanin: Structures, Mechanisms, Controllability., International Journal of Molecular Sciences., (2017), vol. 18(9):1901. 14 pages.
Cadieux et al., The Mannoprotein Cig1 supports iron acquisition from heme and virulence in the pathogenic fungus Cryptococcus neoformans., Journal of Infectious Diseases., (2013), pp. 1339-1347, vol. 207(8).
Camacho et al., N-acetylglucosamine affects Cryptococcus neoformans cell-wall composition and melanin architecture., Microbiology., (2017), pp. 1540-1556, vol. 163.

(56) References Cited

OTHER PUBLICATIONS

Casadevall et al., Fungal melanins differ in planar stacking distances., PLoS One., (2012), vol. 7:e30299. 6 pages.
Chaskes et al., Pigment production by Cryptococcus neoformans from para- and ortho-Diphenols: effect of the nitrogen source., Journal of Clinical Microbiology., (1975), pp. 509-514, vol. 1(6).
Chatterjee et al., Demonstration of a common indole-based aromatic core in natural and synthetic eumelanins by solid-state NMR., Organic and Biomolecular Chemistry., (2014), pp. 6730-6736, vol. 12.
Chatterjee et al., Solid-state NMR Reveals the Carbon-based Molecular Architecture of Cryptococcus neoformans Fungal Eumelanins in the Cell Wall., J Biol Chem., (2015), pp. 13779-13790, vol. 290(22).
Chatterjee et al., The melanization road more traveled by: precursor substrate effects on melanin synthesis in cell-free and fungal cell systems., Journal of Biological Chemistry., (2018), pp. 20157-20168, vol. 293(52).
Chatterjee et al., Using solid-state NMR to monitor the molecular consequences of Cryptococcus neoformans melanization with different catecholamine precursors., Biochemistry., (2012), pp. 6080-6088, vol. 51(31).
Chi et al., Proteomic and bioinformatic characterization of the biogenesis and function of melanosomes. Journal of Proteome Research., (2006), pp. 3135-3144, vol. 5(11).
Christensen et al., Melanization immune responses in mosquito vectors., Trends Parasitol., (2005), pp. 192-199, vol. 21(4).
Chun et al., A major role for capsule-independent phagocytosis-inhibitory mechanisms in mammalian infection by Cryptococcus neoformans., Cell Host & Microbe., (2011), pp. 243-251, vol. 9(3).
Clancy et al., Ultrastructural organization of eumelanin from Sepia officinalis measured by atomic force microscopy., Biochemistry., (2001), pp. 13353-13360, vol. 40(44).
Clarke et al., Integrated Activity and Genetic Profiling of Secreted Peptidases in Cryptococcus neoformans Reveals an Aspartyl Peptidase Required for Low pH Survival and Virulence., PLoS Pathogens., (2016), vol. 12:e1006051. 30 pages.
Cordero et al., Functions of fungal melanin beyond virulence., Fungal Biology Reviews., (2017), pp. 99-112, vol. 31(2).
Cordero et al., Impact of Yeast Pigmentation on Heat Capture and Latitudinal Distribution., Current Biology., (2018), pp. 2657-2664, vol. 28(16).
Cordero et al., Microbial melanins for radioprotection and bioremediation. Microbial Biotechnology. (2017), 10(5), 1186-1190.
Cordero., Melanin for space travel radioprotection., Environmental Microbiology., (2017), pp. 2529-2532, vol. 19(7).
Dadachova et al., The radioprotective properties of fungal melanin are a function of its chemical composition, stable radical presence and spatial arrangement. Pigment Cell Melanoma Res. (2007), 21;192-199.
Dange et al., Blm10 protein promotes proteasomal substrate turnover by an active gating mechanism., Journal Biological Chemistry., (2011), pp. 42830-42839, vol. 286(50).
D'Ischia et al., Chemical and structural diversity in eumelanins: unexplored bio-optoelectronic materials., Angewandte Chemie International Edition England., (2009), pp. 3914-3921, vol. 48(22).
D'Ischia et al., Melanins and melanogenesis: methods, standards, protocols., Pigment Cell Melanoma Research., (2013), pp. 616-633, vol. 26.
D'Souza et al., Cyclic AMP-dependent protein kinase controls virulence of the fungal pathogen Cryptococcus neoformans., Molecular Cell Biology., (2001), pp. 3179-3191, vol. 21(9).
Eisenman et al., Microstructure of cell wall-associated melanin in the human pathogenic fungus Cryptococcus neoformans., Biochemistry., (2005), pp. 3683-3693, vol. 44(10).
Eisenman et al., Synthesis and assembly of fungal melanin., Applied Microbiology and Biotechnology., (2012), pp. 931-940, vol. 93.
Eisenman et al., Vesicle-associated melanization in Cryptococcus neoformans., Microbiology., (2009), pp. 3860-3867, vol. 155.

Fankhauser et al., Identification of GPI anchor attachment signals by a Kohonen self-organizing map., Bioinformatics., (2005), pp. 1846-1852, vol. 21(9).
Foderaro et al., MCC/Eisosomes Regulate Cell Wall Synthesis and Stress Responses in Fungi., Journal of Fungi (Basel)., (2017), vol. 3(4):61. 18 pages.
Franzen et al., Morphometric and densitometric study of the biogenesis of electron-dense granules in Fonsecaea pedrosoi., FEMS Microbiology Letters., (1999), pp. 395-402, vol. 173(2).
Franzen et al., Ultrastructural characterization of melanosomes of the human pathogenic fungus Fonsecaea pedrosoi., Journal of Structural Biology., (2008), pp. 75-84, vol. 162(1).
Gaigg et al., Synthesis of sphingolipids with very long chain fatty acids but not ergosterol is required for routing of newly synthesized plasma membrane ATPase to the cell surface of yeast., Journal of Biological Chemistry., (2005), pp. 22515-22522, vol. 280(23).
Garcia-Rivera et al., Comparative analysis of Cryptococcus neoformans acid-resistant particles generated from pigmented cells grown in different laccase substrates., Fungal Genetics and Biology., (2005), pp. 989-999, vol. 42(12).
Geddes et al., Secretome profiling of Cryptococcus neoformans reveals regulation of a subset of virulence-associated proteins and potential biomarkers by protein kinase A., BMC Microbiology., (2015), vol. 15:206.
Gomez et al., Melanin and fungi. Current Opinion on Infectious Diseases., (2003), pp. 91-96, vol. 16.
Grossman et al., Membrane potential governs lateral segregation of plasma membrane proteins and lipids in yeast., EMBO J., (2007), pp. 1-8, vol. 26(1).
Groux-Degroote et al., Glycolipid-dependent sorting of melanosomal from lysosomal membrane proteins by lumenal determinants., Traffic. , (2008), pp. 951-963, vol. 9.
Gueymard et al., Proposed reference irradiance spectra for solar energy systems testing. Solar Energy. (2002) vol. 73, No. 6, pp. 443-467.
Hegnauer et al., Ultrastructure of native and synthetic Agaricus bisporus melanins. Implications as to the compartmentation of melanogenesis in fungi., Experimental Mycology., (1985), pp. 221-229, vol. 9(3).
Hill., The function of melanin or six blind people examine an elephant., Bioessays., (1992), pp. 49-56, vol. 14.
Homer et al., Intracellular Action of a Secreted Peptide Required for Fungal Virulence., Cell Host & Microbe., (2016), pp. 849-864, vol. 19(6).
Hommel et al., Titan cells formation in Cryptococcus neoformans is finely tuned by environmental conditions and modulated by positive and negative genetic regulators., PLoS Pathogens., (2018), vol. 14:e1006982. 38 pages.
Hong et al., Progressive fuzzy cation-pi assembly of biological catecholamines., Sci Adv., (2018), vol. 4(9):eaat7457. 11 pages.
Hu et al., Transcriptional regulation by protein kinase A in Cryptococcus neoformans., PLoS Pathogens., (2007),vol. 3:e42. 18 pages.
Huffnagle et al., Down-regulation of the afferent phase of T cell-mediated pulmonary inflammation and immunity by a high melanin-producing strain of Cryptococcus neoformans., Journal of Immunology., (1995), pp. 3507-3516, vol. 155.
Ito., The IFPCS presidential lecture: a chemist's view of melanogenesis., Pigment Cell Research., (2003), pp. 230-236, vol. 16.
Jung et al., (2009) Role of ferroxidases in iron uptake and virulence of Cryptococcus neoformans., Eukaryotic Cell., (2009), pp. 1511-1520, vol. 8.
Kwon-Chung et al., Utilization of indole compounds by Cryptococcus neoformans to produce a melanin-like pigment. Journal of Clinical Microbiology., (1983), pp. 1419-1421, vol. 18(6).
Liu et al., Isolation and biophysical studies of natural eumelanins: applications of imaging technologies and ultrafast spectroscopy., Pigment Cell Research., (2003), pp. 606-618, vol. 16.
Liu et al., Systematic genetic analysis of virulence in the human fungal pathogen Cryptococcus neoformans., Cell., (2008), pp. 174-188, vol. 135(1).
Łopusiewicz., The isolation, purification and analysis of the melanin pigment extracted from Armillaria mellea rhizomorphs., World Scientific News., (2018), pp. 135-153, vol. 100.

(56) References Cited

OTHER PUBLICATIONS

Ludvigsen et al., Three-dimensional structure in solution of barwin, a protein from barley seed. Biochemistry., (1992), pp. 8783-8789, vol. 31.
Martinez et al., Susceptibility of Cryptococcus neoformans biofilms to antifungal agents in vitro., Antimicrobial Agents and Chemotherapy., (2006), pp. 1021-1033, vol. 50(3).
Meredith et al., Radiative relaxation quantum yields for synthetic eumelanin. Photochemistry and Photobiology, (2004), 79(2): 211-216.
Meredith et al., The physical and chemical properties of eumelanin., Pigment Cell Research., (2006), pp. 572-594, vol. 19(6).
Momen-Heravi et al., Current methods for the isolation of extracellular vesicles., Biological Chemistry., (2013), pp. 1253-1262, vol. 394(10).
Mulholland et al., Ultrastructure of the yeast actin cytoskeleton and its association with the plasma membrane., Journal of Cellular Biology., (1994), pp. 381-391, vol. 125(2).
Nosanchuk et al., Budding of melanized Cryptococcus neoformans in the presence or absence of L-dopa., Microbiology., (2003), pp. 1945-1951, vol. 149.
Nosanchuk et al., Cellular charge of Cryptococcus neoformans: contributions from the capsular polysaccharide, melanin, and monoclonal antibody binding., Infectious Immunology., (1997), pp. 1836-1841, vol. 65(5).
Nosanchuk et al., Impact of melanin on microbial virulence and clinical resistance to antimicrobial compounds., Antimicrobial Agents and Chemotherapy., (2006), pp. 3519-3528, vol. 50(11).
Nosanchuk et al., The contribution of melanin to microbial pathogenesis., Cell Microbiology., (2003), pp. 203-223, vol. 5.
Oliveira et al., Cryptococcus neoformans cryoultramicrotomy and vesicle fractionation reveals an intimate association between membrane lipids and glucuronoxylomannan., Fungal Genetics & Biology., (2009), pp. 956-963, vol. 46(12).
O'Meara et al., Interaction of Cryptococcus neoformans Rim101 and protein kinase A regulates capsule., PLoS Pathogens., (2010), vol. 6(2):e1000776.
Pacelli et al., Melanin is effective in protecting fast and slow growing fungi from various types of ionizing radiation. Environmental Microbiology (2017) 19(4), 1612-1624.
Panepinto et al., The cell biology of virulence—lessons from the pathogenic fungus Cryptococcus neoformans., Communicating Current Research and Educational Topics and Trends in Applied Microbiology., (2007), A. Méndez-Vilas (Ed.) FORMATEX. 10 pages.
Panzella et al., The Late Stages of Melanogenesis: Exploring the Chemical Facets and the Application Opportunities. Int J Mol Sci., (2018), vol. 19(6):1753. 16 pages.
Perez-Dulzaides et al., Cell-wall dyes interfere with cryptococcus neoformans melanin deposition. Microbiology (2018) 164:1012-1022.
Pombeiro-Sponchiado et al., Production of Melanin Pigment by Fungi and it's Biotechnological Applications. Melanin. 2017. 47-75.
Prados-Rosales et al., Structural Characterization of Melanin Pigments from Commercial Preparations of the Edible Mushroom Auricularia auricula., Journal of Agricultural Food Chemistry., (2015) pp. 7326-7332, vol. 63(33).
Prota., Progress in the chemistry of melanins and related metabolites., Medicinal Research Reviews., (1988), pp. 525-556, vol. 8(4).
Riesz et al., Quantitative scattering of melanin solutions., Biophysical Journal., (2006), pp. 4137-4144, vol. 90(11).
Rodrigues et al., Extracellular vesicles produced by Cryptococcus neoformans contain protein components associated with virulence., Eukaryotic Cell., (2008), pp. 58-67, vol. 7(1).
Rodrigues et al., Vesicular mechanisms of traffic of fungal molecules to the extracellular space., Current Opinion in Microbiology., (2013), pp. 414-420, vol. 16(4).
Rodrigues et al., Vesicular polysaccharide export in Cryptococcus neoformans is a eukaryotic solution to the problem of fungal trans-cell wall transport., Eukaryotic Cell., (2007), pp. 48-59, vol. 6(1).
San-Blas et al., Cladosporium carrionii and Hormoconis resinae (C. resinae): cell wall and melanin studies., Current Microbiology., (1996), pp. 11-16, vol. 32.
Sarna et al., Identification and characterization of melanin in tissues and body fluids., Folia Histochemica Cytochemica., (1978), pp. 275-286, vol. 16(4).
Sealy et al., Eumelanins and pheomelanins: characterization by electron spin resonance spectroscopy., Science., (1982), pp. 545-547, vol. 217(4559).
Seiji et al., Chemical composition and terminology of specialized organelles (melanosomes and melanin granules) in mammalian melanocytes., Nature., (1963), pp. 1082-1084, vol. 197.
Solano., Melanin and Melanin-related polymers as materials with biomedical and biotechnological applications—cuttlefish ink and mussel foot proteins as inspired biomolecules., International Journal of Molecular Sciences., (2017), vol. 18(7): 1561. 18 pages.
Steenbergen et al., Cryptococcus neoformans interactions with amoebae suggest an explanation for its virulence and intracellular pathogenic strategy in macrophages., Proc Natl Acad Sci U S A., (2001), pp. 15245-15250, vol. 98(26).
Stoetzner et al., The morphology of Cryptococcus neoformans in human cryptococcosis. A light-,phase-contrast and electron-microscopic study., Mycopathol et Mycologica Applicata., (1971), pp. 327-335, vol. 45.
Tajima et al., Solubilized melanin suppresses macrophage function., FEBS Open Bio., (2019), pp. 791-800, vol. 9(4).
Tsirilakis et al., Methylxanthine inhibit fungal chitinases and exhibit antifungal activity., Mycopathologia., (2012), pp. 83-91, vol. 173.
Upadhyay et al., Subcellular Compartmentalization and Trafficking of the Biosynthetic Machinery for Fungal Melanin., Cell Rep., (2016), pp. 2511-2518, vol. 14(11).
Walker et al., Melanin externalization in Candida albicans depends on cell wall chitin structures., Eukaryotic Cell., (2010), pp. 1329-1342, vol. 9(9).
Walker et al., The Viscoelastic Properties of the Fungal Cell Wall Allow Traffic of AmBisome as Intact Liposome Vesicles., MBio., (2018), vol. 9(1):e02383-17. 15 pages.
Walton et al., Novel gene functions required for melanization of the human pathogen Cryptococcus neoformans., Molecular Microbiology., (2005), pp. 1381-1396, vol. 57(5).
Wang et al., Cryptococcus neoformans melanin and virulence: mechanism of action., Infection and Immunity., (1995), pp. 3131-3136, vol. 63(8).
Wang et al., Growth of Cryptococcus neoformans in presence of L-dopa decreases its susceptibility to amphotericin B., Antimicrob Agents Chemother., (1994), pp. 2648-2650, vol. 38(11).
Wang et al., Melanin, melanin "ghosts," and melanin composition in Cryptococcus neoformans. Infect Immun., (1996), pp. 2420-2424, vol. 64(7).
Wang et al., WdChs4p, a homolog of chitin synthase 3 in Saccharomyces cerevisiae, alone cannot support growth of Wangiella (Exophiala) dermatitidis at the temperature of infection., Infection and Immunity., (1999), pp. 6619-6630, vol. 67(12).
Watt et al., The supramolecular structure of melanin. Soft Matter, (2009), 5, 3754-3760.
White., Melanin: a naturally occurring cation exchange material., Nature., (1958), pp. 1427-1428, vol. 182.
Wikipedia.com Hydrochloric Acid. Dec. 19, 2018. Retrieved from the internet Jun. 15, 2022. 10 pages.
Wolf et al., Interaction of Cryptococcus neoformans extracellular vesicles with the cell wall., Eukaryotic Cell., (2014), pp. 1484-1493, vol. 13(12).
Xiao et al., Elucidation of the hierarchical structure of natural eumelanins., J R Soc Interface., (2018), vol. 15(140) 10 pages.
Zajac et al., The fundamental unit of synthetic melanin: a verification by tunneling microscopy of X-ray scattering results., Biochim Biophys Acta., (1994), pp. 271-278, vol. 1199(3).
Zhang et al., Cryptococcal phosphoglucose isomerase is required for virulence factor production, cell wall integrity and stress resistance. FEMS Yease Research, (2015), 15, fov072. 9 pages.

(56) References Cited

OTHER PUBLICATIONS

Zhong et al., Following fungal melanin biosynthesis with solid-state NMR: biopolymer molecular structures and possible connections to cell-wall polysaccharides., Biochemistry., (2008), pp. 4701-4710, vol. 47(16).

Zhu et al., Laccase of Cryptococcus neoformans is a cell wall-associated virulence factor., Infection and Immunity., (2001), pp. 5589-5596, vol. 69(9).

* cited by examiner

MELANIN BASED BIO-COMPOSITES FOR 3D PRINTING

CROSS-REFERENCE TO RELATED APPLICATIONS

This claims priority to U.S. Provisional Patent Application No. 62/783,591, filed on Dec. 21, 2018, U.S. Provisional Patent Application No. 62/898,948, filed on Sep. 11, 2019 and U.S. Provisional Patent Application No. 62/898,926, filed on Sep. 11, 2019, the entire contents of each of which are fully incorporated herein by reference.

TECHNICAL FIELD

The present disclosure relates to compositions comprising melanin and methods of making and using thereof.

BACKGROUND OF THE INVENTION

Melanins are exceptional biopolymers capable of interacting and/or absorbing all forms of electromagnetic radiation. This optical capacity derives from their complex molecular organization, including graphite-like structures of phenolic/indolic polymers that form spherical nanoparticles and larger structures thereof. The capacity of melanins to interact with radiation makes them good radiation shielding materials. Most of the absorbed radiation energy by melanin is effectively translated into heat; a property that could be exploited in solar thermal energy systems. In addition, melanin biopolymers are attractive for multiple biotech and biomedical applications including bioelectronics, radioprotection, optics, cosmetics, printing, and drug delivery.

Melanins are present in animals, plants, fungi, and bacteria. Fungi are the richest source, capable of synthesizing melanins from at least three different biosynthetic pathways, utilizing 1,8-dihydroxynapthalene (DHN), tyrosine, or tyrosine derivatives like dihydroxyphenylalanine (DOPA).

Simple and cost-effective melanin extraction methods are needed to produce melanin in large quantities inexpensively so the compound may be used in many commercial applications. Melanotic fungi present rich melanin sources for industrial applications. Multiple fungal species produce melanin constitutively (e.g., *Aureobasidium melanogenum, Wingiella dermititidis*) and others require the provision of a melanin precursor (e.g., *Gliocephalotrichum simplex, Cryptococcus neoformans*). For example, *G. simplex* is a filamentous fungus that secretes a tyrosinase enzyme and, when grown in media supplemented with L-Tyrosine, it produces significant amounts of extracellular melanin nanoparticles. Similarly, *C. neoformans* is a perfectly spherical yeast of 2-15 nm in diameter that can produce a melanin coat surrounding its cell wall via the oxidation of exogenous phenolic compounds (e.g., dopamine, DOPA, epinephrine, methyl-DOPA) by a laccase enzyme. This melanin coat is formed by a connected network of melanin nanoparticles of 30-60 nm in diameter.

SUMMARY OF THE INVENTION

The present invention is directed to ultraviolet and visible light absorbing biocomposites comprising a thermoplastic polymer, a thermoplastic elastomer, a metal, silicone, and combinations thereof and melanin.

The present invention is also directed to articles comprising the biocomposite described herein, and methods of making and using the articles comprising the biocomposite.

The present invention is further directed to a filament for 3-dimensional (3D) printing, methods for making and using the filament, and 3D printed items.

Other aspects of the invention will become apparent by consideration of the detailed description and accompanying drawings.

BRIEF DESCRIPTION OF THE DRAWINGS

FIG. 1A shows an example of L-DOPA melanized *Cryptococcus* yeast liquid culture. FIG. 1B is a light microscopy negative-stained (India ink) image of a *Cryptococcus* yeast cell with a melanized cell wall (inner black circle) surrounded by a polysaccharide capsule (outer white layer) that excludes the ink particles in background. Scale bar, 10 μm. FIG. 1C shows a micrograph of isolated *Cryptococcus* melanin using the extraction methods of the present invention. Scale bar, 10 μm. FIG. 1D shows a scanning electron micrograph revealing rounded hollow micron sized particles. FIG. 1E is an image of one gram of dried *Cryptococcus* melanin exhibiting a dark/opaque appearance due to its high light absorbance.

FIG. 3A shows a radiographic film exposed to UV (1 min) or visible light (1 s) revealing the amount of light shielding/attenuated by of two circular disks made of PLA or PLA+melanin (*Cryptococcus* melanin) at 10% (m/m). The mean gray value is quantified in FIG. 3B. FIG. 3C shows thermal images of both disks after exposure to visible light (581,000 LUX for 10 min; ambient temperature 4° C.). The temperature was quantified and shown in FIG. 3D.

FIG. 4A shows the shielding of UV light by PLA disks containing a different concentration (0, 0.1, 1, 10% w/w) of *Cryptococcus* melanin. The graph shows the quantification of color change as modal gray value. Bars represent minimal and max modal values. FIG. 4B shows the visible (top) and infrared (bottom) images and the average temperature values of disks following irradiation with a white LED lamp for 10 minutes.

FIG. 11A is a visible image of 50 mg of melanin samples loaded in a 48-well microtiter plate. FIG. 11B shows the infrared images of samples before and after 12-minute irradiation and a graph of the mean temperature values. Error bars depict maximum and minimum temperature values.

FIG. 14A is thermal images of 3D-printed objects following 2- and 8-minute exposures to white LED lamp (LUX 75,000). FIG. 14B is a graph of the temperature of objects as a function of time. The presence of melanin increases the heat absorbing properties of PLA.

DETAILED DESCRIPTION OF THE INVENTION

Figure 1A:
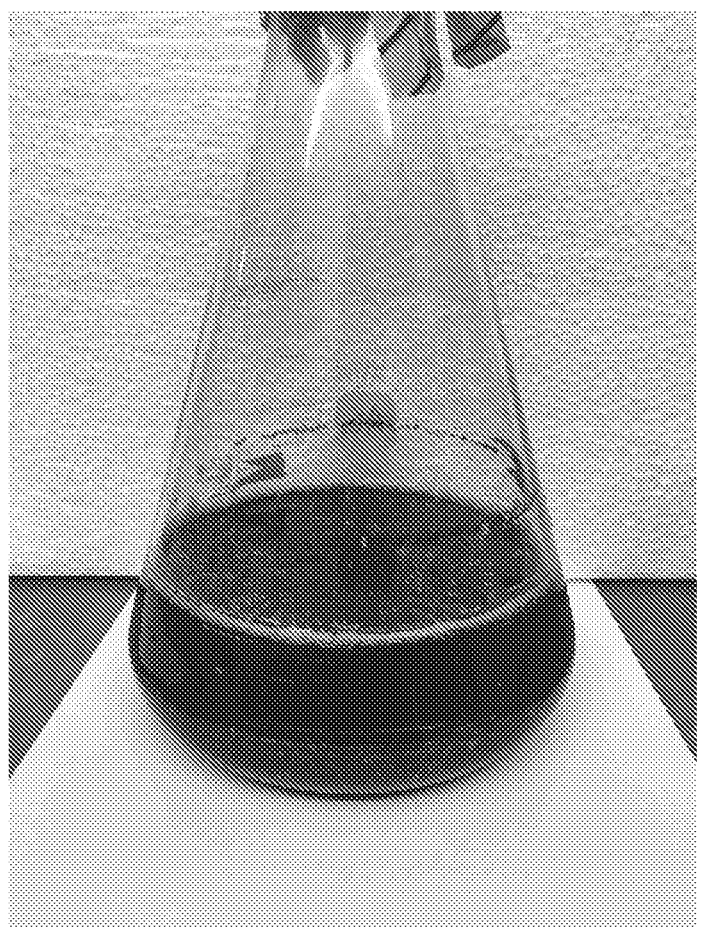
FIGS. 1A-1E illustrate microscopic characteristics of cell wall-associated melanin from *C. neoformans*.

Disclosed herein are biocomposites comprising melanin which absorb ultraviolet and visible light. Articles produced from the biocomposite possess UV/visible light shielding and heat absorbing properties. The biocomposite was formulated for 3D printing filaments and 3D printed items made from the filaments exhibit similar broad-spectrum UV/visible light shielding and heat absorbing properties

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of," and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The terms "ultraviolet" and "UV" are used herein to mean electromagnetic radiation, especially solar electromagnetic radiation, with a wavelength from about 100 nm to about 400 nm, and includes the UV-A, UV-B, and UV-C sub-classifications of such radiation. The term "UV-A" means ultraviolet electromagnetic radiation with a wavelength from about 320 nm to about 400 nm and includes UV-A1 (from about 340 nm to about 400 nm) and UV-A2 (from about 320 nm to about 340 nm). The term "UV-B" means ultraviolet electromagnetic radiation with a wavelength from about 290 nm to about 320 nm. The term "UV-C" means ultraviolet electromagnetic radiation with a wavelength from about 200 nm to about 290 nm.

The term "UV absorber" refers to an article or composition that absorbs, scatters, and/or reflects UV radiation.

A "reference" refers to a standard or control conditions such as a sample or surface that is free, or substantially free, of an agent such as melanin.

"Inconel," as used herein, refers to austenitic nickel-chromium-based superalloys. Inconel alloys may vary in their compositions, but all are predominantly (>40%) nickel, with between 10 and 35% chromium as the second most abundant element. Other components include molybdenum, iron, niobium, tantalum, cobalt, manganese, copper, aluminum, titanium, silicon, carbon, sulfur, phosphorus, and boron in minor amounts.

Any compositions or methods provided herein can be combined with one or more of any of the other compositions and methods provided herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

2. BIOCOMPOSITE COMPOSITIONS

The present disclosure provides biocomposite compositions. The biocomposite compositions comprise melanin and a thermoplastic polymer, a thermoplastic elastomer, a metal, silicone, or combinations thereof. The biocomposite may absorb ultraviolet and visible light. The biocomposite compositions may comprise at least about 1% by weight melanin.

a) 3D Printable Materials

The biocomposite may include a thermoplastic polymer, a thermoplastic elastomer, a metal, silicone, and combinations thereof. The thermoplastic polymer, thermoplastic elastomer, metal, silicone, and combinations thereof may be 3D printable materials.

Thermoplastic polymers are polymers that become pliable at elevated temperatures and solidify upon cooling. Thermoplastic polymers include, for example, poly(methyl methacrylate) (PMMA), acrylonitrile butadiene styrene (ABS), polyamides (nylon), polylactic acid (PLA), polybenzimidazole, polycarbonate, polyether sulfone (PES), polyetherether ketone (PEEK), polyetherimide (PEI), polyethylene (PE), polyphenylene oxide (PPO), polypropylene (PP), polyvinyl chloride (PVC), and polytetrafluoroethylene (PTFE). In some embodiments, the thermoplastic polymer comprises acrylonitrile butadiene styrene (ABS), acrylic styrene acrylonitrile (ASA), nylon, polycarbonate, polyethylene terephthalate, polylactic acid (PLA), polypropylene or combinations thereof. In exemplary embodiments, the thermoplastic polymer comprises polylactic acid.

Thermoplastic elastomers (TPEs) are copolymers of a plastic and a rubber such that they consist of materials with thermoplastic and elastomeric properties. Thermoplastic elastomers are also referred to as thermoplastic rubbers. TPEs include, for example, sytrenic block copolymers, thermoplastic polyurethanes, and thermoplastic copolyester.

In some embodiments, the metal comprises aluminum, cobalt chrome, Inconel, stainless steel, titanium, tool steel, or combinations thereof.

The 3D printable materials may be up to 99.99% by weight of the biocomposite. In some embodiments, the biocomposite may comprise at least 80% by weight of the 3D printable materials, at least 85% by weight of the 3D printable materials, at least 90% by weight of the 3D printable materials, at least 95% by weight of the 3D printable materials, at least 96% by weight of the 3D printable materials, at least 97% by weight of the 3D printable materials, at least 98% by weight of the 3D printable materials, or at least 99% by weight of the 3D printable materials. In certain embodiments, the biocomposite may comprise between 80% and 99.99% by weight of the 3D printable materials.

The biocomposite may additionally comprise other components, including but not limited to plasticizers, strengtheners, fillers, flame retardants, antioxidants, colorants, antimicrobials, thickeners and antistatic agents. Plasticizers include materials that may increase flexibility and/or elasticity (e.g., acetyl tributylcitrate, epoxidized soybean oil, polyethylene glycole (PEG)). Strengtheners include materials that may increase impact resistance (e.g., carbon nanotubes, graphene). Fillers include materials that may are used to give the plastic more mass (e.g., lignin, carbon fibers, hemp, minerals like mica, clay, wollastonite, calcium sulfate, calcium carbonate, talc, silica, glass, alumina trihydrate). Flame Retardants include materials prevent fires, or slow the spread of a fire (e.g., organic chloride, organic bromide, antimony trioxide, magnesium hydroxide, aluminum hydroxide, silicon). Antimicrobials include materials that may help the plastic to resist microbial growth (e.g., tetracycline). Thickeners include materials that may increase the viscosity of the plastic (e.g., cellulose). Antistatics include materials that may prevent the buildup of static electricity.

b) Fungal Melanins

The biocomposite may include at least about 0.01% by weight melanin. In some embodiments, the biocomposite comprises at least about 0.1% by weight melanin, at least about 0.5% by weight melanin, at least about 1% by weight melanin, at least about 2% by weight melanin, at least about 3% by weight melanin, at least about 4% by weight melanin, at least about 5% by weight melanin, at least about 6% by weight melanin, at least about 7% by weight melanin, at least about 8% by weight melanin, at least about 9% by weight melanin, at least about 10% by weight melanin, at least about 11% by weight melanin, at least about 12% by weight melanin, at least about 13% by weight melanin, at least about 14% by weight melanin, or at least about 15% by weight melanin. The biocomposite may contain between 0.01% and 15% by weight melanin, between 0.1% and 15% by weight melanin, between 1% and 15% by weight melanin, between 1% and 10% by weight melanin, between 1% and 5% by weight melanin, between 5% and 15% by weight melanin, between 10% and 15% by weight melanin, or between 5% and 10% by weight melanin. In certain embodiments, the biocomposite comprises between 1% and 10% by weight melanin.

The melanin may be any pure form of melanin. The melanin may comprise melanin purified from biological sources, synthetic melanin, metal-complexed forms of melanin, or combinations thereof.

Metal-complexed forms of melanin occur when melanin is contacted with a source of metal ions resulting in various types of binding. For example, carboxyl or phenolic groups of the melanin will generally participate in ion-exchange type reactions by binding with metal ions and releasing hydrogen ions. Oxygen-containing groups of the melanin, including phenolic and alcoholic hydroxyl, carbonyl and methoxy groups, as well as amine groups, may also be involved in bonding to form metal-organic complexes possibly in the form of chelates. Metal-complexed forms of melanin may include metals such as copper, manganese, boron, tin, aluminum, zinc, nickel, cobalt and cadmium, as well as calcium, magnesium and sodium, and mixtures thereof.

Melanin in nature is typically in a granular form, and is often associated with proteins, lipids and other cellular components. The usual method of preparing soluble melanin is to extract it into cold or hot alkali, precipitate it with acid, and hydrolyze proteins, carbohydrates, and lipids away from it by prolonged refluxing in aqueous acid, e.g., 6 N HCl. The melanin can be further purified away from lipids and the like by washing with an organic solvent, e.g., ethanol, ether or tetrahydrofuran, to remove lipid or wax-like materials, optionally alternated with additional hydrolysis in hot acid.

The purified melanin residue which is recovered can then be dried and/or suspended or dissolved or otherwise combined with an appropriate medium.

In general, use of alkali to solubilize the melanin causes changes in melanin polymeric structure. Preferably, the melanin used for the present invention is melanin which has retained at least a portion of its polymeric structure such that the melanin is still insoluble.

c) Method of Purifying Melanin

Figure 8:
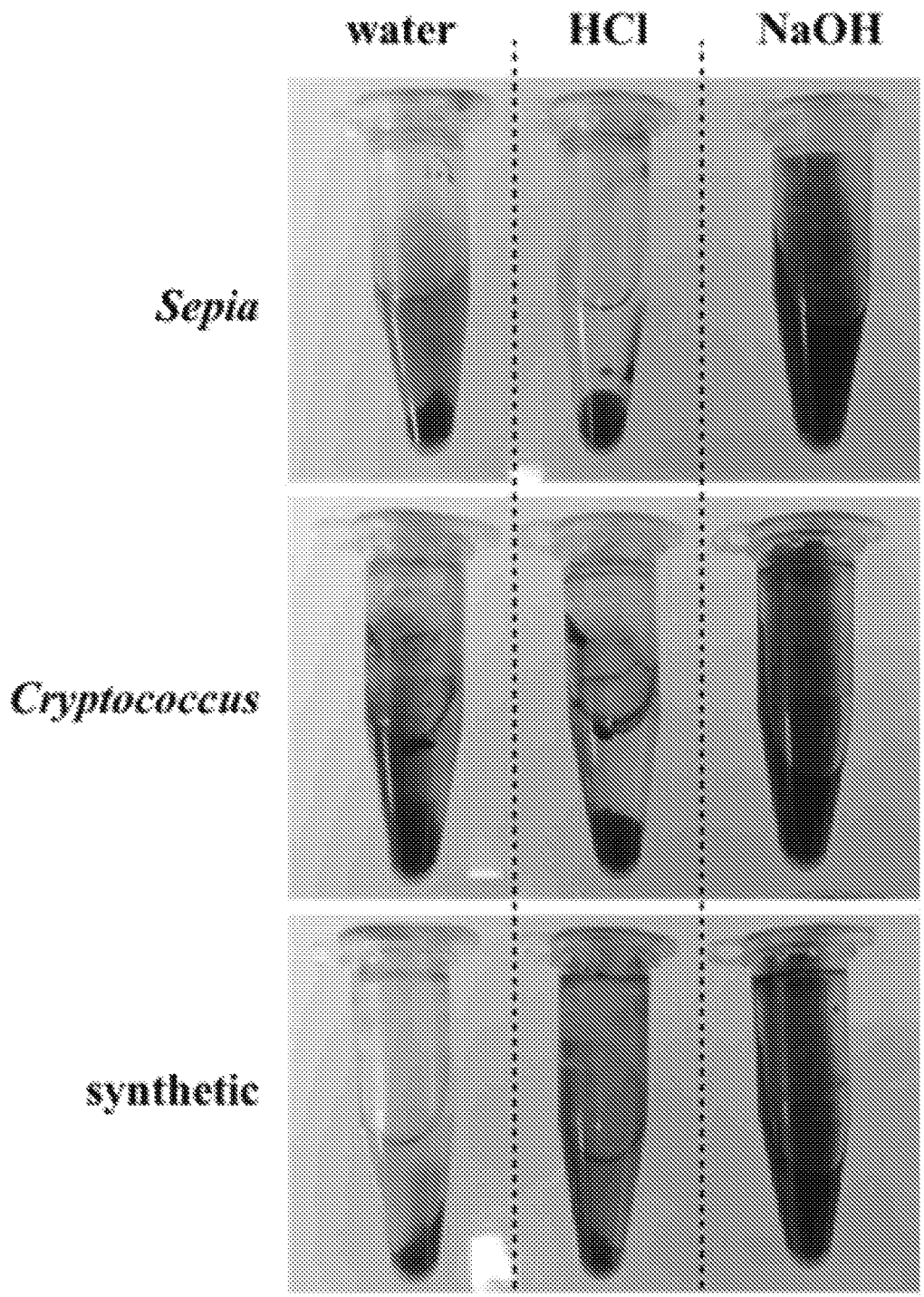
FIG. 8 is images showing the susceptibility of melanin to alkaline conditions. Sepia, *Cryptococcus* and synthetic melanin were suspended in water, 6 N HCl or 1 M NaOH at 1 mg/mL. Samples were incubated at 37° C.' for 6 days. Tubes were centrifuged at 13,000 rpm for 2 minutes and photographed. Melanins are defined as insoluble in aqueous conditions, hence the relative transparency of supernatants in samples incubated in water or HCl. However, the dark appearance of samples incubated in NaOH demonstrates that the melanin higher-order structure is degraded into more soluble components. Note that *Cryptococcus* melanin isolated using the protocol described herein is relatively more stable in water and HCl than Sepia and synthetic melanin, respectively.

Melanin used in the biocomposite described herein was purified from a melanin producing fungus. The method is a shorter version of a cell-wall isolation protocol was used that produces similar yields in shorter time at lower extraction costs. The method does not include an alkali incubation step, known to compromise melanin higher-order structure (FIG. 8). The method is summarized in Table 1 and described in U.S. Provisional Patent No. 62/783,591, the contents of which are herein incorporated herein by reference.

TABLE 1

Cell wall-associated melanin isolation comparison between prior art and the method used herein.

| Cell Wall-Associated Melanin Isolation | Cell Wall-Associated Melanin Isolation of the Present Invention |
| --- | --- |
| 1. Enzyme digestion of melanized fungi during 24 hours at 30° C.<br>2. 4M guanidine thiocyanate for 12 hours at room temperature<br>3. Proteinase K for 4 hours at 65° C.<br>4. Folch extraction method (Chloroform:methanol:aqueous saline) mixture as 8:4:3. Repeat step for a total of 3 consecutive times.<br>5. Boiling in 6N HCl for 2 hours. | 1. Boiling in 6N HCl for 2 hours<br>2. Folch extraction method (Chloroform:methanol:aqueous saline) mixture as 8:4:3. Repeat step for a total of 3 consecutive times.<br>3. Let to air dry. Material can be wash with pure water. |

The method for purifying the melanin comprises the step of heating a melanin producing fungus in 6N HCl and extracting the melanin using a chloroform:methanol:saline mixture.

The melanin producing fungus may be any of those fungal species known in the art to produce melanin either constitutively or under melanin producing conditions. In some embodiments, the melanin producing fungus is selected from the group consisting of *Cryptococcus neoformans, Aureobasidium melanogenum, Wingiella dermititidis, Cryomyces antarcticus* and *Cryptococcus* chs3, *Cryptococcus* csr2, *Cryptococcus* pgi1, modified cell wall mutants thereof, *Exophiala dermatitidis, Agaricus biscporus, Cladosporium sphaerospermum*, and combinations thereof.

The heating step may have a temperature in the range of 60° C. to 120° C. In some embodiments the heating step has a temperature of at least 60° C., at least 65° C., at least 70° C., at least 75° C., at least 80° C., at least 85° C., at least 90° C., at least 95° C., at least 100° C., at least 105° C., at least 110° C., or at least 115° C. In some embodiments the heating step has a temperature less than 120° C., less than 115° C., less than 110° C., less than 105° C., less than 100° C., less than 95° C., less than 90° C., less than 85° C., less than 80° C., less than 75° C., less than 70° C., or less than 65° C.

The heating step may have a duration of 30 minutes to 24 hours. In some embodiments, the heating step may have a duration of about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In certain embodiments, the heating step may have a duration from 30 minutes to 3 hours, from 30 minutes to 2.5 hours, from 30 minutes to 2 hours, from 30 minutes to 1.5 hours, from 30 minutes to 1 hour, from 1 hour to 3 hours, from 1 hour to 2.5 hours, from 1 hour to 2 hours, or from 1 hour to 1.5 hours.

The chloroform:methanol:saline mixture may be any mixture useful in the removal of lipids from a sample. In some embodiments, the mixture is about 8 parts chloroform:4 parts methanol:and 3 parts saline by volume.

3. ARTICLES COMPRISING MELANIN BIOCOMPOSITE COMPOSITIONS

The present disclosure provides articles comprising the biocomposite described herein. The article can include any hardened objects including helmets, pill bottles, food packaging, building materials (e.g., roofing and/or siding materials, hardscape materials, and the like), lamps, sunshades, photoelectric devices, and materials for vehicles including military, air, and space craft, containers for plants, seeds, drugs, biological materials, radioactive materials, and the like, fabrics, umbrellas, eye-glass frames, cases for electronics, or armor, clothing, or equipment used for shielding specific body parts. The hardened objects may be 3D-printed. The articles may be used in radiation shielding or harvesting technologies, bioelectronics or bioremediation.

a) Radiation Energy Capture/Shielding

Solar absorbers are substances that convert energy from the sun into heat, hence minimizing energy investments. Melanotic yeasts can capture heat from electromagnetic radiation, a property that can be exploited for solar thermal energy technologies. The heat absorption capacity of fungal melanins when exposed to UV, visible, and infrared frequencies can be applied in solar thermal technologies (e.g., solar heating, solar thermal electricity generation, solar thermoelectric, and solar thermophotovoltaics).

Due to the broadband optical absorption of melanins, surfaces in close contact with melanin or containing melanin can be heated up passively or without the need to spend energy. Melanin-assisted heating can be mixed or applied in spacecraft's surfaces, paintings, lacquers, coatings or construction materials in extraterrestrial spaces for passive heating. Melanin biocomposites and articles made from the biocomposites, as described herein, may be used as solar absorbers.

The use of melanotic microorganisms is also attractive given the ability of some species to survive extreme environmental conditions (cold, salt, radiation, extracellular space) and grow in the form of melanotic biofilms which can be used to coat multiple surfaces.

The increase of ultraviolet radiation makes the application of UV shielding materials more urgent. Currently, UV shielding agents commonly used in the market are classified into two types: organic ultraviolet shielding agents and inorganic ultraviolet shielding agents. The former is most commonly divided into benzophenones, salicylates, benzotriazoles and triazines, such as Tinuvin, Tinuvin P and Tinuvin 1577. Organic UV shielding agents are highly effective at absorbing ultraviolet light. However, it has problems such as poor compatibility and poor thermal stability to varying degrees. At the same time, small molecules migrate and degrade as the use time prolongs, resulting in a decrease in ultraviolet shielding performance and eventually failure. The inorganic ultraviolet shielding agent mainly uses the absorption and scattering of ultraviolet rays to achieve the effect of ultraviolet shielding, and the common ones are nano TiO2 and nano ZnO. The inorganic ultraviolet shielding agent has good light and heat stability, but often cannot be compatible with the polymer matrix, and easily causes the system to be opaque. At the same time, the photocatalytic activity of the inorganic ultraviolet shielding agent is generally strong, and the polymer matrix is easily degraded.

The present invention provides an ultraviolet shielding biocomposite material comprising melanin in combination with the advantages of 3D printable materials, such that the biocomposite has excellent UV shielding and absorption with good mechanical properties and ease of forming articles of any desired size and shape.

Due to the microwave shielding capacity of *C. neoformans* cell-wall melanin, external microwave melanin shielding can be applied for military defense applications. Melanin-containing surfaces will be thermally protected from microwave irradiation.

The biocomposite and articles disclosed herein preserve the radiation energy capture properties of melanin in a hardened article that can be designed in the preferred size and shape necessary for the desired use or function.

b) Methods of Making Melanin Biocomposite

Methods for making the melanin biocomposite include those appropriate for use with thermoplastics, thermoplastic elastomers, silicone, or metals, including injection molding, extrusion, calendaring, film blowing, blow molding, rotational molding, compression molding, casting, and 3D printing.

In some embodiments, the method of making the melanin biocomposite comprises melting the thermoplastic polymer, thermoplastic elastomer, metal, silicone, and combinations thereof, adding powdered melanin to the melted thermoplastic polymer, thermoplastic elastomer, metal, silicone, and combinations thereof gradually with mixing to form a melted biocomposite material, shaping the melted biocomposite material to form the article, and cooling the article.

In some embodiments, the method of making the melanin biocomposite comprises combining a powder form of the thermoplastic polymer, thermoplastic elastomer, metal, silicone, and combinations thereof and powdered melanin to form a biocomposite powder, dehydrating the biocomposite powder, heating the biocomposite powder to create melted biocomposite material, extruding the melted biocomposite material to form a filament for use in 3D printing, melting the filament in a printing head of a 3D printer to form melted biocomposite, and depositing melted biocomposite in successive layers to form the article.

4. 3D PRINTING

The present disclosure also provides a filament for 3D printing. The filament may comprise a 3D printable material selected from the ground consisting of a thermoplastic polymer, a thermoplastic elastomer, a metal, silicone, and combinations thereof, and melanin.

The 3D printable materials may be up to 99.99% by weight of the filament. In some embodiments, the filament may comprise at least 80% by weight of the 3D printable materials, at least 85% by weight of the 3D printable materials, at least 90% by weight of the 3D printable materials, at least 95% by weight of the 3D printable materials, at least 96% by weight of the 3D printable materials, at least 97% by weight of the 3D printable materials, at least 98% by weight of the 3D printable materials, or at least 99% by weight of the 3D printable materials. In certain embodiments, the filament may comprise between 80% and 99.99% by weight of the 3D printable materials.

Thermoplastic polymers are polymers that become pliable at elevated temperatures and solidify upon cooling. Thermoplastic polymers include, for example, poly(methyl methacrylate) (PMMA), acrylonitrile butadiene styrene (ABS), polyamides (nylon), polylactic acid (PLA), polybenzimidazole, polycarbonate, polyether sulfone (PES), polyetherether ketone (PEEK), polyetherimide (PEI), polyethylene (PE), polyphenylene oxide (PPO), polypropylene (PP), polyvinyl chloride (PVC), and polytetrafluoroethylene (PTFE). In some embodiments, the thermoplastic polymer comprises acrylonitrile butadiene styrene (ABS), acrylic styrene acrylonitrile (ASA), nylon, polycarbonate, polyethylene terephthalate, polylactic acid (PLA), polypropylene or combinations thereof. In exemplary embodiments, the thermoplastic polymer comprises polylactic acid.

Thermoplastic elastomers (TPEs) are copolymers of a plastic and a rubber such that they consist of materials with thermoplastic and elastomeric properties. Thermoplastic elastomers are also referred to as thermoplastic rubbers. TPEs include, for example, sytrenic block copolymers, thermoplastic polyurethanes, and thermoplastic copolyester.

In some embodiments, the metal comprises aluminum, cobalt chrome, Inconel, stainless steel, titanium, tool steel, or combinations thereof.

The filament may include at least about 0.01% by weight melanin. In some embodiments, the filament comprises at least about 0.1% by weight melanin, at least about 0.5% by weight melanin, at least about 1% by weight melanin, at least about 2% by weight melanin, at least about 3% by weight melanin, at least about 4% by weight melanin, at least about 5% by weight melanin, at least about 6% by weight melanin, at least about 7% by weight melanin, at least about 8% by weight melanin, at least about 9% by weight melanin, at least about 10% by weight melanin, at least about 11% by weight melanin, at least about 12% by weight melanin, at least about 13% by weight melanin, at least about 14% by weight melanin, or at least about 15% by weight melanin. The filament may contain between 0.01% and 15% by weight melanin, between 0.1% and 15% by weight melanin, between 1% and 15% by weight melanin, between 1% and 10% by weight melanin, between 1% and 5% by weight melanin, between 5% and 15% by weight melanin, between 10% and 15% by weight melanin, or between 5% and 10% by weight melanin. In certain embodiments, the filament comprises between 1% and 10% by weight melanin.

The melanin may be any pure form of melanin. The melanin may comprise melanin purified from biological sources, synthetic melanin, metal-complexed forms of melanin, or combinations thereof. The melanin may be purified from melanin producing fungus as described in Section 2(c) and further described in U.S. Provisional Patent Appln. Nos. 62/783,591 and 62/898,948, to which this application claims priority.

The filament may additionally comprise other components, including but not limited to plasticizers, strengtheners, fillers, flame retardants, antioxidants, colorants, antimicrobials, thickeners and antistatic agents. Plasticizers include materials that may increase flexibility and/or elasticity (e.g., acetyl tributylcitrate, epoxidized soybean oil, polyethylene glycole (PEG)). Strengtheners include materials that may increase impact resistance (e.g., carbon nanotubes, graphene). Fillers include materials that may are used to give the plastic more mass. The filament may comprise at least one filler including, but not limited to, metal, metal oxide, metal nitride, metal carbide, carbon compound, silicon compound, boron compound such as boron nitride, ceramic materials, natural fibers or the combinations thereof. The filler may be diamond material other than detonation diamond, graphite, carbon black, carbon fiber, graphene, oxidized graphene, carbon soot, carbon nanotube, pyrolytic carbon, silicon carbide, aluminum carbide, carbon nitride, lignin, carbon fibers, hemp, minerals like mica, clay, wollastonite, calcium sulfate, calcium carbonate, talc, silica, glass, alumina trihydrate or the combinations thereof. Flame Retardants include materials prevent fires, or slow the spread of a fire (e.g., organic chloride, organic bromide, antimony trioxide, magnesium hydroxide, aluminum hydroxide, silicon). Antimicrobials include materials that may help the plastic to resist microbial growth (e.g., tetracycline). Thickeners include materials that may increase the viscosity of the plastic (e.g., cellulose). Antistatics include materials that may prevent the buildup of static electricity.

The filament can be transparent or substantially transparent. The filament may also comprise a coloring agent, to make the filament available in a desired color.

The present disclosure further provides methods of making the filament, using the filament in 3D printing, and 3D printed items.

In some embodiments, methods of making the filament comprise combining a powder form of the thermoplastic polymer, thermoplastic elastomer, metal, silicone, and combinations thereof and powdered melanin to form a powder mixture, dehydrating the powder mixture, heating the powder mixture to create a melted powder mixture, and extruding the melted powder mixture to form a filament for use in 3D printing.

In some embodiments, methods of making the 3D printed item comprise melting the filament in a printing head of a 3D printer and depositing the melted filament material in successive layers to form the article.

5. EXAMPLES

Example 1

Production and Purification of Fungal Melanin

Growth and melanization of C. neoformans. C. neoformans Serotype A strain H99 (ATCC 208821) was precultured from frozen stocks in Sabouroaud dextrose liquid media for 2 days at 30° C. (shaking at 180 rpm). Pigmentation of C. neoformans cultures were prepared by inoculating a final concentration of $10^5$ cells/mL to sterile filtered minimal media (15 mM dextrose, 10 mM $Mg_2SO_4$, 29.3 mM $KH_2PO_4$, 13 mM glycine, 3 mM thiamine-HCL; adjusted to pH 5.5) with or without 1 mM supplementation of each pigment precursor: L-DOPA, methyl-DOPA, dopamine hydrochloride, norepinephrine, epinephrine, serotonin. Yeast cultures are grown under dark conditions for 5 days at 30° C. and shaking at 180 rpm. Yeast cells were then washed three times with PBS by decanting the supernatant after centrifugation (15 min at 6,000 rpm). The resulting melanized yeast concentrated slurry can be processed to isolate the cell wall-associated melanin, lyophilized to form bioflakes or poured on surfaces to form biofilm coat.

Melanized "bioflakes". Melanized yeast cells are collected by centrifugation, washed three times with PBS by centrifugation. Yeast pellets are freeze at −20° C. and lyophilized in a freeze-drying system (Labconco, Kansas City, MO).

Figure 1B:
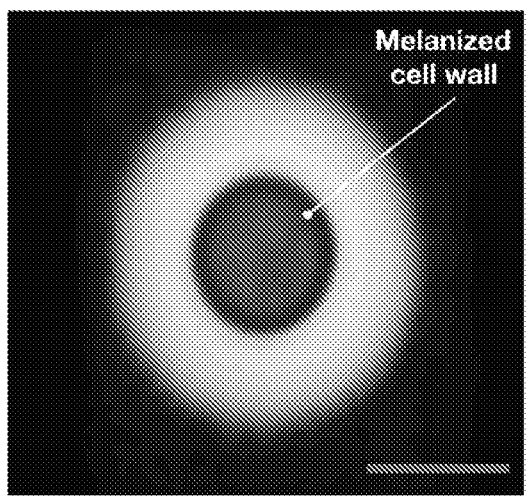
Figure 1C:
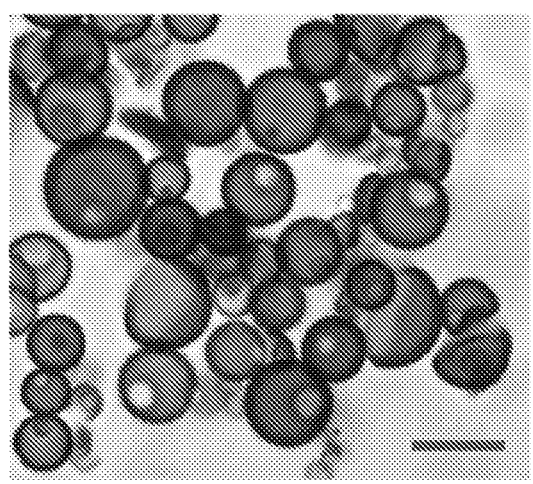
Figures 1D, 1E:
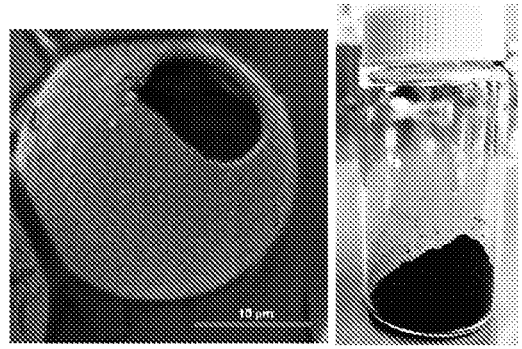

Isolating Melanin from the Cell Wall. The two-step process of the present invention is performed without the conventional steps of Enzyme digestion, 4M guanidine thiocyanate, and proteinase K as shown in Table 1. The two-step process begins by growing the fungi in a growth medium such as 15 mM dextrose, 10 mM $Mg_2SO_4$, 29.3 mM $KH_2PO_4$, 13 mM glycine, 3 mM thiamine-HCL; adjusted to pH 5.5 with or without 1 mM supplementation of each pigment precursor (e.g. L-DOPA) for 2-14 days (FIG. 1A). Melanized yeast cells (FIG. 1B) are collected by centrifugation and subjected to acid hydrolysis followed by an organic extraction consisting of 8:4:3 mixture of chloroform:methanol:aqueous saline. The process recovers cell wall-associated melanin in the form of microshells (FIG. 1C & FIG. 1D). These melanin microshells exhibit a broadband monotonic absorption spectra which is typical to melanins covering the whole solar irradiance range (FIG. 1F).

One liter of melanized C. neoformans culture was harvested by centrifugation (15 min at 4,500 rpm) and washed twice with PBS. The yeast pellet was suspended with equal volume of 6 N HCl and incubated 1 hr at 100° C. Hydrolyzed material was washed three times with PBS and subjected to 3 consecutive Folch lipid extractions maintaining final mixtures to 8:4:3 chloroform:methanol:saline-solution. The methanol-aqueous upper fraction containing melanin was collected and centrifuged at 4,000 for 5 mins. The precipitated melanin pellet is set to air dry resulting in a packed pellet. Alternatively, the extracted melanin particles can be dialyzed against distilled water overnight and lyophilized in a freeze-drying system (Labconco, Kansas City, MO).

Example 2

Preparing a Biocomposite of Polylactic Acid and Fungal Melanin

A composite material of melanin mixed with polylactic acid (PLA), a biodegradable thermoplastic was prepared by melting the thermoplastic with mixing until a smooth consistency and adding melanin powder gradually over time to ensure a homogeneous mixture was formed. After cooling the mixture, the thermoplastic resin hardened.

To create the PLA disks, as shown in FIGS. 2-6, PLA was cut into ~1-2 cm lengths and placed into silicone baking molds. The molds were heated to 200-210° C. to allow the PLA to melt. As melting continued the plastic was mixed with forceps to achieve even heating. Melanin at 10% by weight of PLA was measured and folded into the melted PLA in aliquots of 100-500 µg. Subsequent aliquots were added once the preceding aliquot was homogeneously mixed into the PLA. A flat silicone mat was used to press the biocomposite resin into flat disks. Following cooling, the melanin thermoplastic disks were removed from the silicone molds.

Figure 2:
FIG. 2 shows an image of PLA and PLA+melanin circular disks of one embodiment of the invention. Disks dimensions: 1.5-inch diameter and ~0.15-inch thick.

The melanin-PLA composite is dark black, compared to a pure PLA disk of the same dimensions (FIG. 2).

Example 3

Melanin-PLA Composite Light Shielding/Absorption Effects

The composites made as detailed in Example 2 were tested for their ability to shield against and absorb ultraviolet and visible light (FIG. 3A-3D).

Figure 3A:
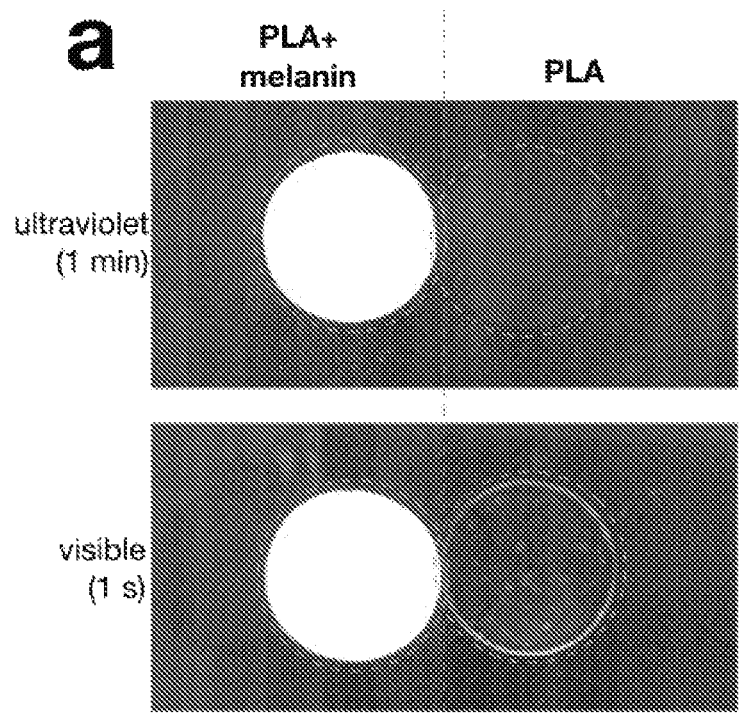
FIGS. 3A-3D show the ability of one embodiment of a melanin-PLA biocomposite to shield and capture light.
Figure 3B:
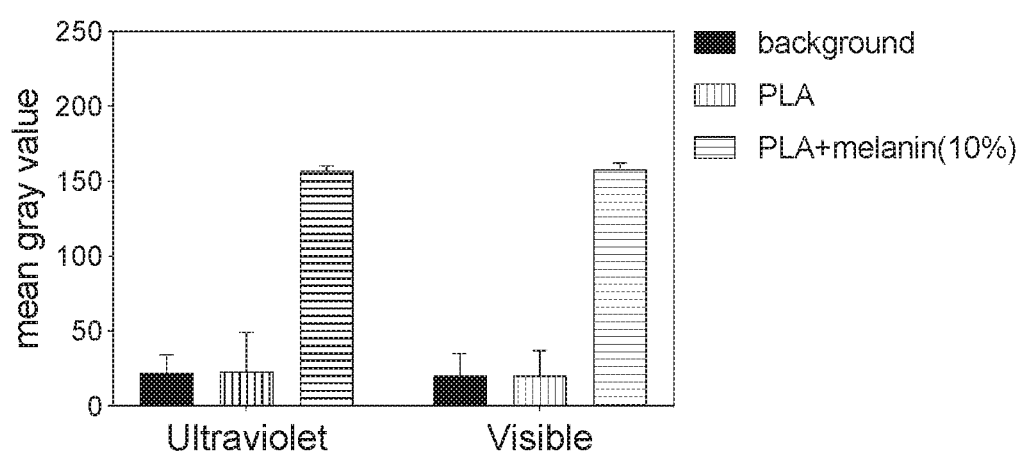

Disks were placed on top of a radiography film and irradiated for 1 minute with a ~280 nm UV lamp inside a Faraday box designed to control light intensity or 1 second of visible light (FIG. 3A). Following irradiations, the film was developed and digitally scanned to quantify the change in color intensity on shielded areas, lighter color means more shielding. The graph in FIG. 3B shows the quantification of color change as mean gray value.

Figure 3C:
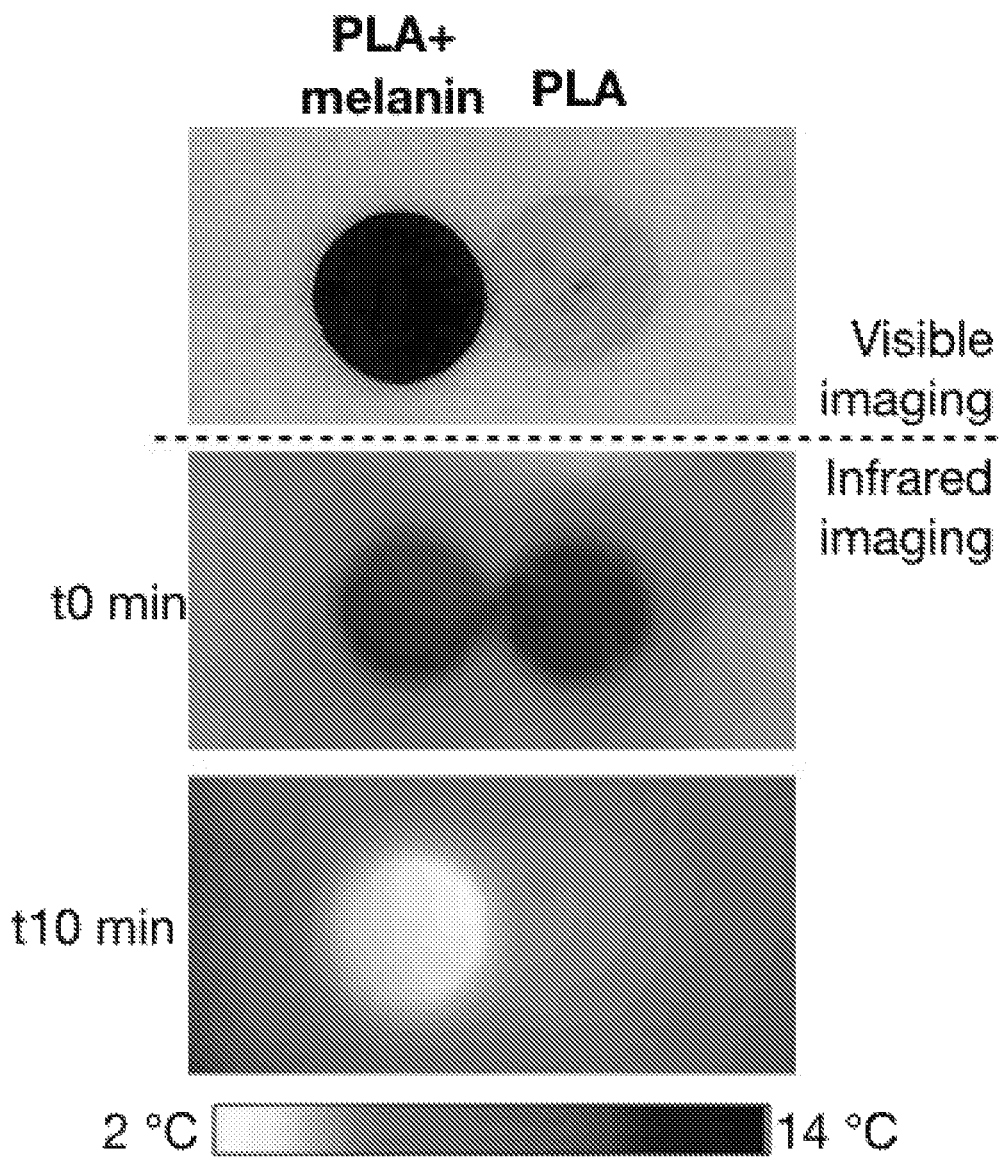
Figure 3D:
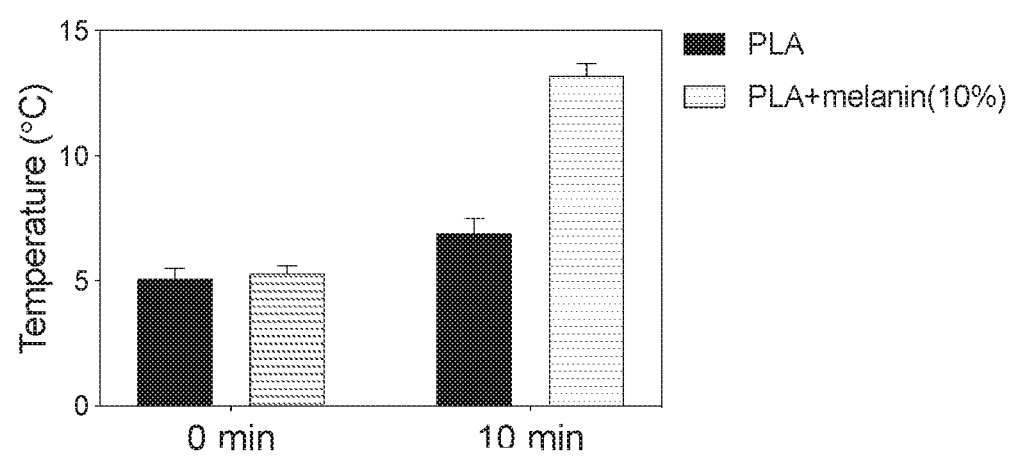

Thermal imaging of the disks was done prior to and after exposure to visible light (581,000 LUX) for 10 minutes at ambient temperature (FIG. 3C). The temperature was determined by thermal imagining and quantitated as shown in FIG. 3D.

Example 4

Effects of Melanin Concentration of Melanin-PLA Composite Characteristics

4 PLA disks were generated containing 0, 0.1, 1, and 10% melanin isolated from *Cryptococcus* cell-walls using the method described above. Ten grams of PLA was heated to ~210° C. in a cylindrical silicone mold and melted. The corresponding amount of melanin was added to the melted plastic and repeatedly folded to achieve a homogeneous mixture. The mold was then removed from heat and allowed to cool before removing the Melanin-PLA composite disc.

Figure 4A:
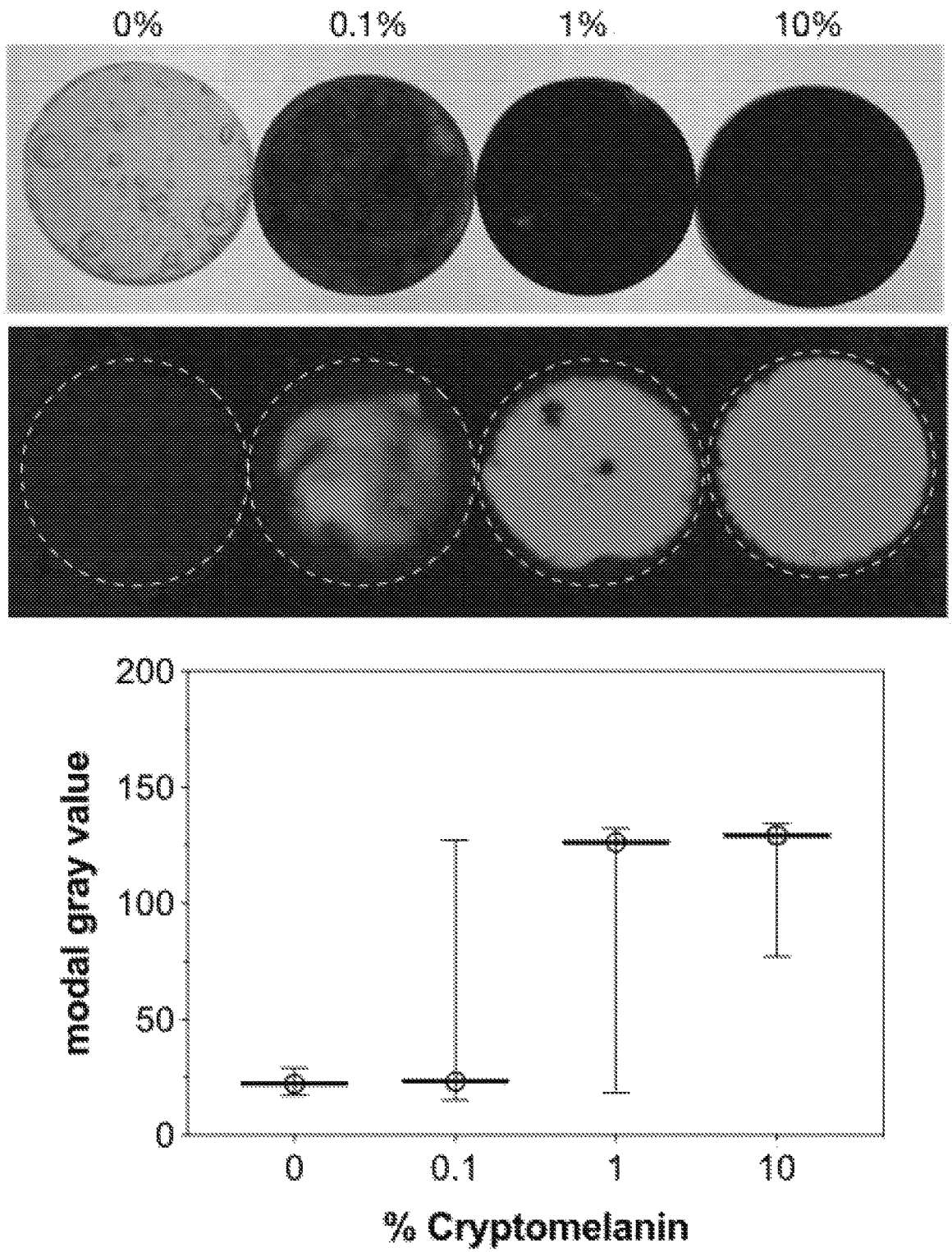
FIGS. 4A-4B show the shielding and heat capture of Melanin-PLA biocomposite disks as a function of melanin concentration.
Figure 4B:
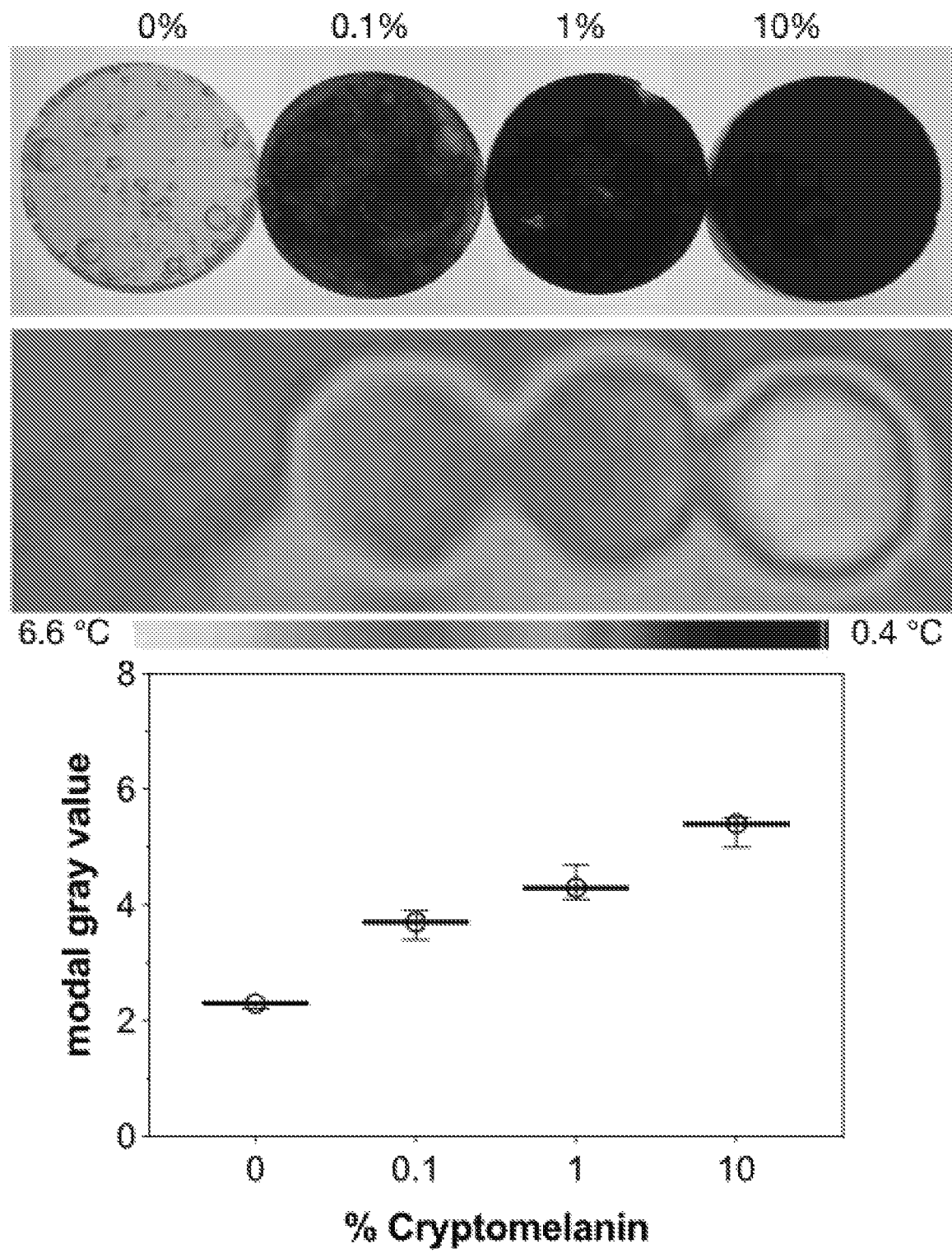

The disks were placed on top of a radiography film and irradiated for 2 minutes with a ~280 nm UV lamp inside a Faraday box designed to control light intensity. Following irradiations, the film was developed and digitally scanned to quantify the change in color intensity on shielded areas, lighter color means more shielding (FIG. 4A). The graph shows the quantification of color change as modal gray value. The modal gray value of developed radiography film shows full shielding at 1% w/w melanin. The dark spots in the 1% disk reflect that the mixing of melanin and melted plastic can be improved. Full shielding was maintained at 10% w/w melanin The discs were cooled at 3° C. and exposed to a white LED lamp for 10 mins. Images show the visible (top) and infrared (bottom) images of disks following irradiation (FIG. 4B). Using thermal imaging the average temperature values were determined and shown in the graph.

These data suggest that at least 1% w/w melanin would be a particularly useful concentration in the biocomposites.

Example 5

Comparison of Melanin Preparations

As described above, alternate methods of melanin isolation are known in the art. Lopusiewicz et al. (*Polymers* 2018, 10, 386) purified melanin from the mushroom *Agaricus* using a method comprising an alkaline hydrolysis step. This alkaline hydrolysis step is known to alter the structure of melanin. A summary of the differences of the melanin preparation is shown in Table 2.

TABLE 2

Differences in Melanin Isolation Methods of the Present Invention and Lopusiewicz

|  | Present Application | Lopusiewicz 2018 |
| --- | --- | --- |
| Melanin Source | Pure cultures of melanotic yeasts (e.g., *Cryptococcus neoformans*) | agricultural waste from the production of *Agaricus biscporus* |
| Hydrolysis (Alkaline/Acid) | NONE<br>acid: 6M HCl (2 h, 90° C.) | alkaline: pH = 10 by 1M NaOH (24 h, 65° C.)<br>acid: 6M HCl (2 h, 90° C.) |
| Organic Solvent Extraction | Folch extraction: chloroform:methanol:saline (8:4:3)3x | Chloroform 3x<br>ethyl acetate 3x<br>ethanol 3x |

Figure 5:
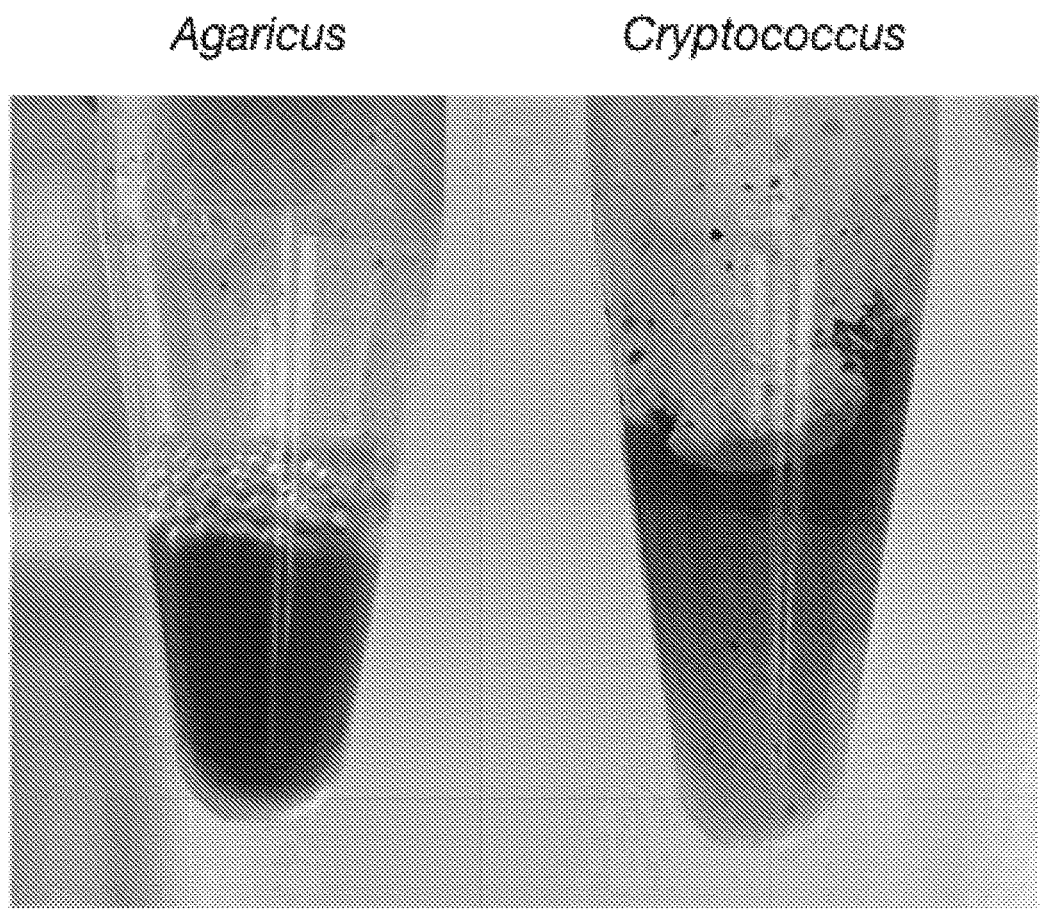
FIG. 5 is an image of purified melanins from *Agaricus* and *Cryptococcus* using purification methods which include and exclude an alkaline hydrolysis step, respectively.

Melanins are known to be insoluble. As shown in FIG. 5, the *Agaricus* melanin purified using the method of Lopusiewicz et al. readily dispersed in water relative to *Cryptococcus* melanin purified as described herein. The low yields of the Lopusiewicz melanin (100 micrograms from 500 grams of mushroom) and the differences in dispersion suggested that degradation of melanin during purification results in a different type of melanin product.

Figure 6:
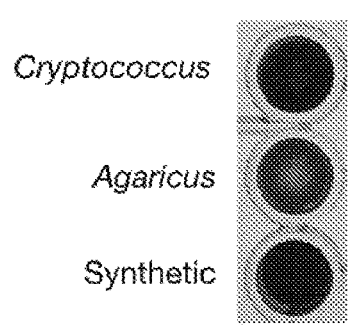
FIG. 6 shows a graph of the optical absorbance as a function of wavelength for three aqueous melanin suspensions purified from *Cryptococcus, Agaricus*, or Sepia melanin. The photograph on the left shows the different color intensity of the aqueous melanin samples.
Figure 6:
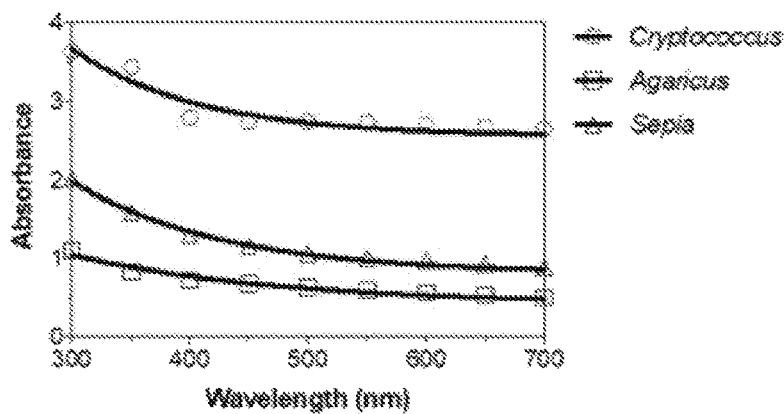

FIG. 6 demonstrates the differences in optical absorption of the three types of melanin, the *Agaricus* melanin purified using the method of Lopusiewicz et al., the *Cryptococcus* melanin purified as described herein and Sepia melanin purchased from Sigma-Aldrich. Aqueous suspensions of melanin at 1 mg/mL were prepared, mixed and analyzed using UV-Vis plate spectrometer Molecular Devices. The data shows that *Cryptococcus* melanin preparations exhibited higher absorbance, particularly at higher wavelengths, followed by Sepia and *Agaricus* melanin, at much lower absorbances.

Figure 7A:
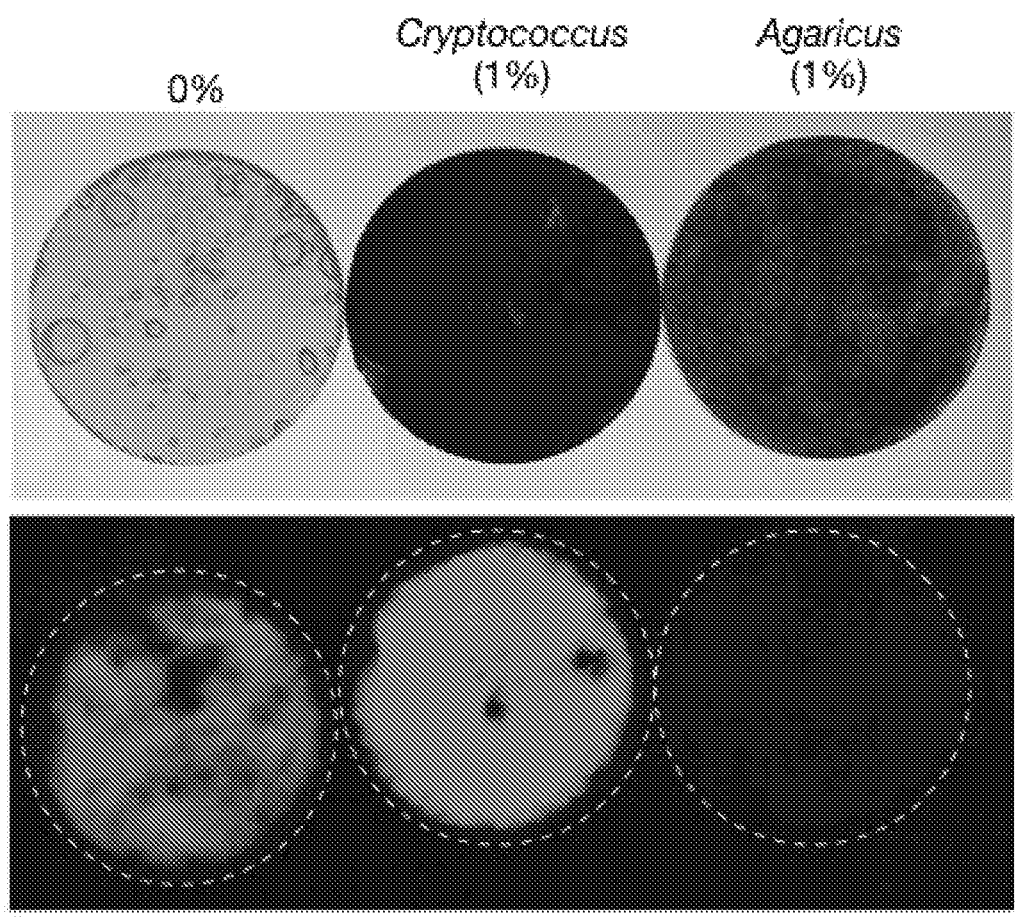
FIGS. 7A and 7B show the shielding (FIG. 7A) and heat capture (FIG. 7B) differences of melanin-PLA composite disks using melanin produced with and without alkaline hydrolysis.
Figure 7A:
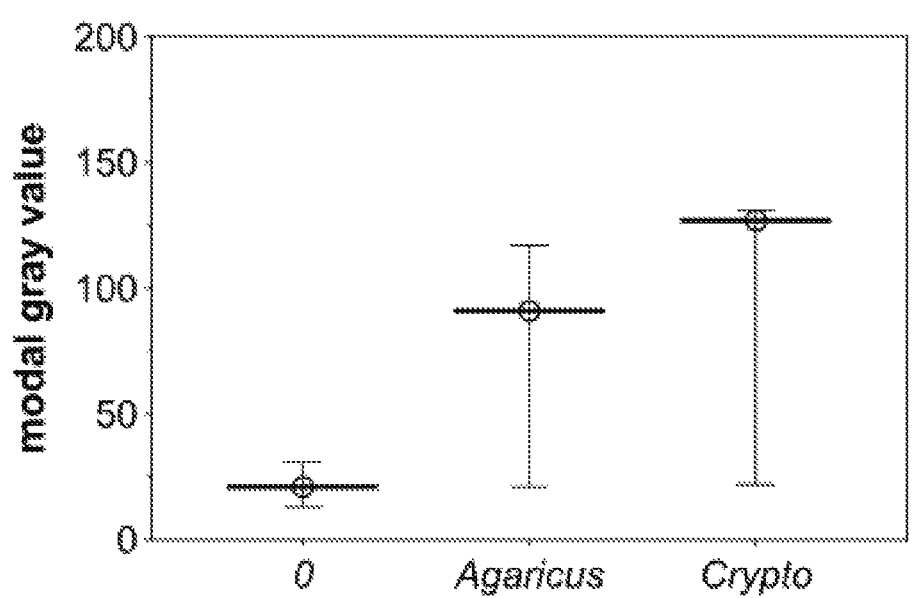
Figure 7B:
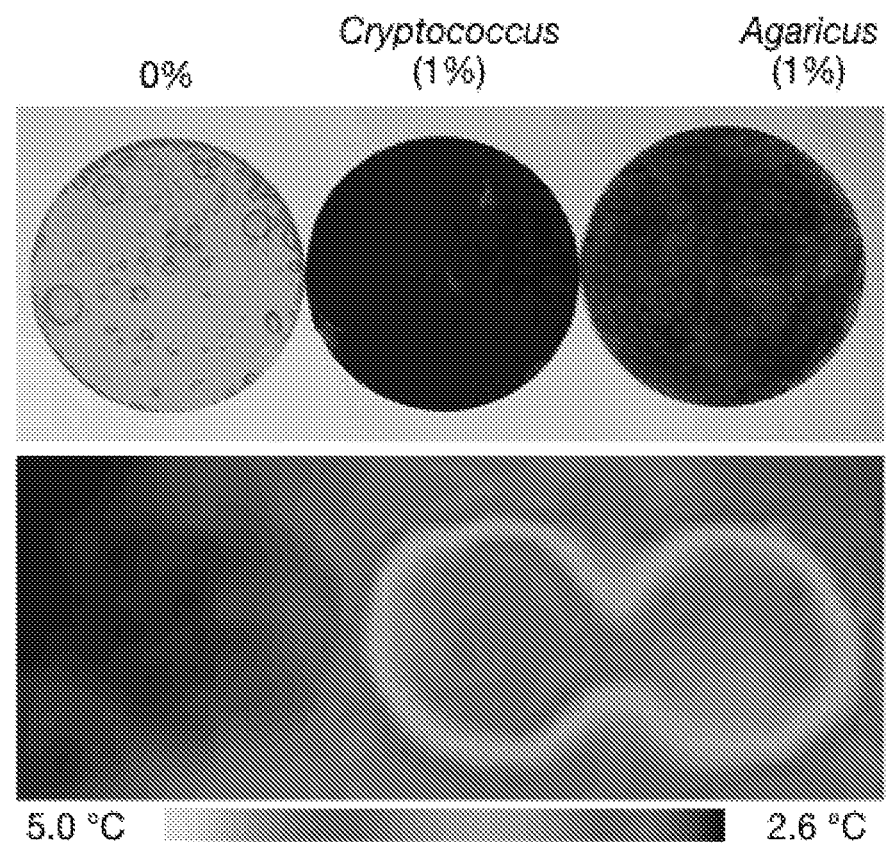

The melanin products from *Cryptococcus* and *Agaricus* were also compared for their ability to shield and capture heat from visible white-light as described in Example 4. As shown in FIGS. 7A-7B, the *Cryptococcus* melanin purified as described herein exhibited higher shielding and heat-absorbing properties. Without being bound by theory, this may be due to the partial degradation of *Agaricus* during purification using an alkaline hydrolysis step.

These data demonstrate the differences in the optical, shielding, and heat absorbing properties between melanin preparations, specifically preparations which were purified using alkaline hydrolysis, such as those described in Lopusiewicz et al.

Example 6

Melanin Biocomposite Filaments

The melanin-PLA composite may be fabricated in the form of a filament, which can be used for standard 3D printing activities. The powdered 3D-printable material and powdered melanin may be mixed together to the desired composition and dehydrated for at least 24-36 hours. The mixture may then be added to a filament extruder as known in the art. Starting at 170° C. the temperature may be adjusted until the desired filament diameter is achieved.

Figure 13:
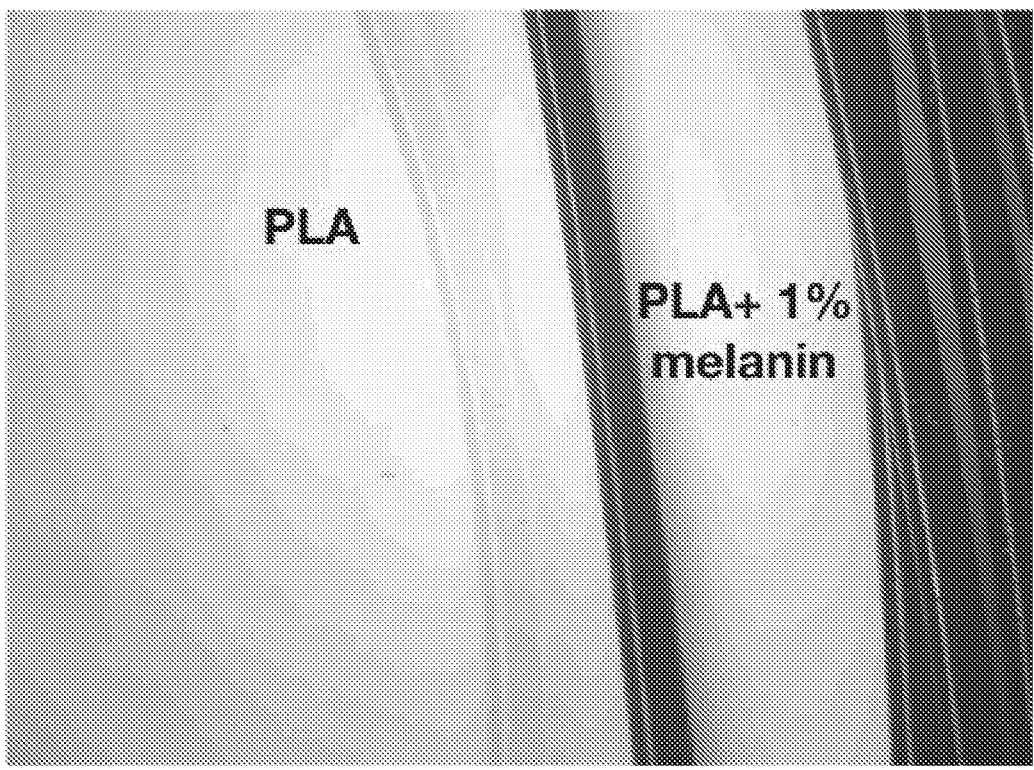
FIG. 13 is an image of two extruded 3D printing filaments; just PLA and PLA+melanin (1% w/w).

FIG. 13 shows an image of an example of a PLA 3D printing filament and a 3D printing filament made of out PLA doped with 1% (w/w) melanin.

Example 7

Purification and Characterization of Melanin from Various Melanotic Fungi

Figure 9:
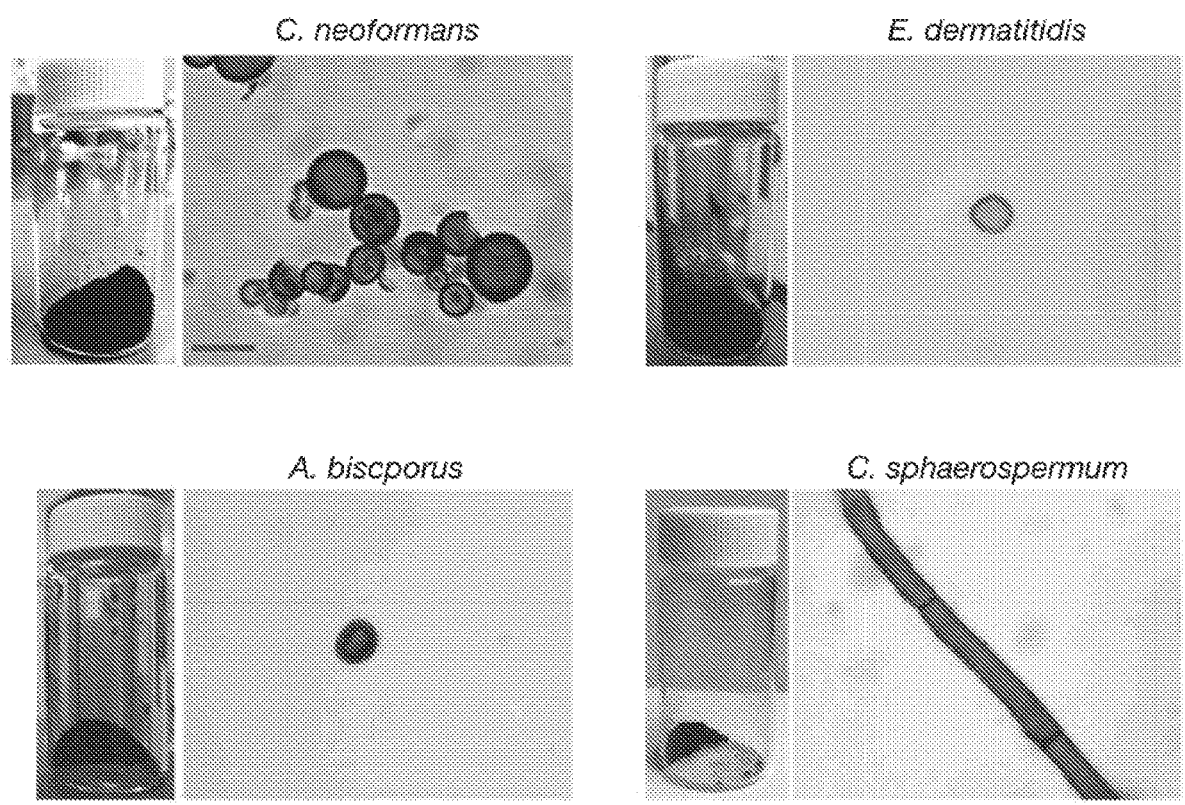
FIG. 9 is light micrographs of melanin isolated from *Cryptococcus neoformans, Exophiala dermatitidis, Agaricus biscporus, Cladosporium sphaerospermum*. Scale bar, 10 μm.

Melanin was isolated from *Exophiala dermatitidis, Agaricus biscporus, Cladosporium sphaerospermum* (FIG. 9). *E. dermatitidis* was grown in Sabouraud's agar plates and incubated at 30° C. *A. biscporus* mushrooms were purchased from the market. The filamentous fungus, *Cladosporium*, was grown in Sabouraud's agar plates and incubated at 24° C. Cells were collected from plates, and melanin isolation was performed as described in Example 1. Similar to *Cryptococcus*, the melanin isolation protocol yielded hollow melanin micrometer size particles for *Exophiala* and *Agaricus*. Melanin isolated from *Cladosporium* had a tubular structure.

Figure 10:
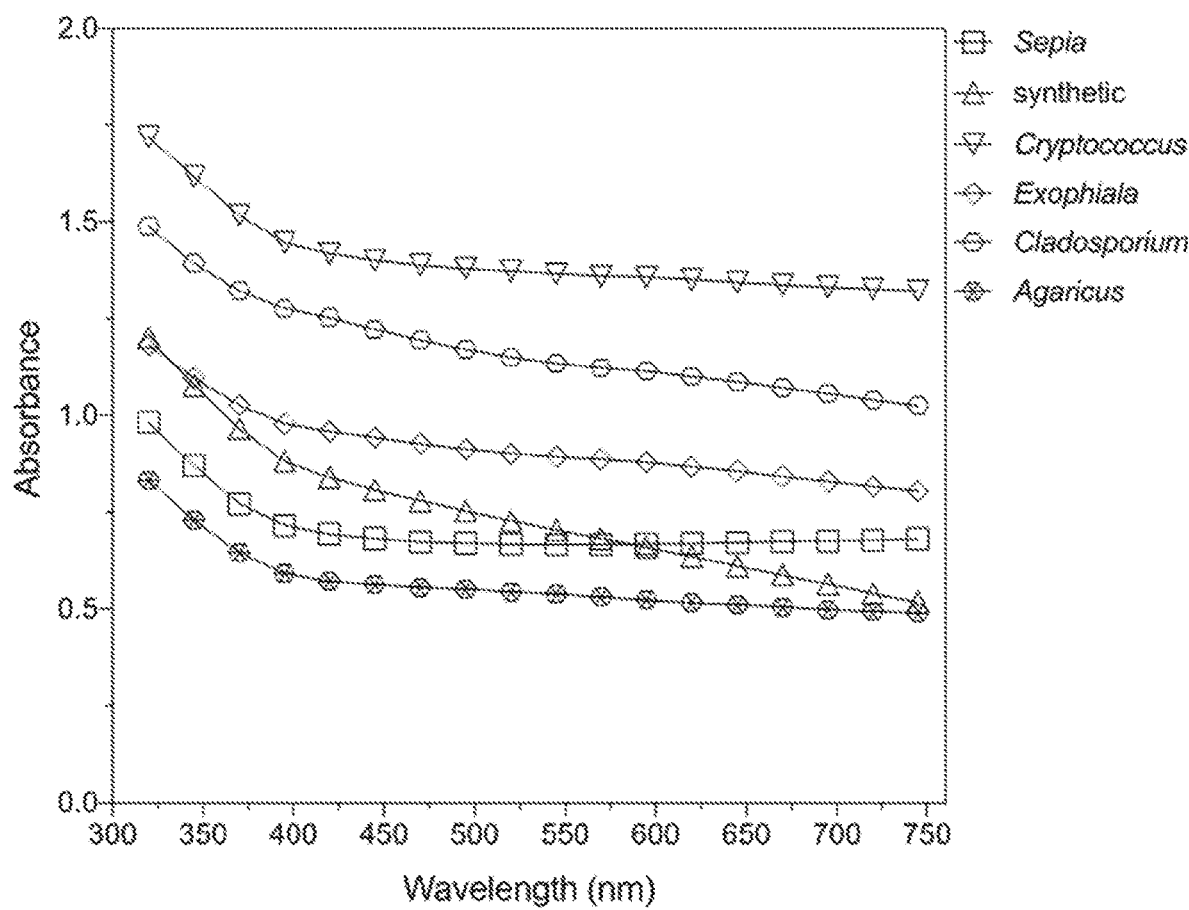
FIG. 10 is a graph of the optical absorption spectra of melanin samples isolated from *Cryptococcus neoformans, Exophiala dermatitidis, Cladosporium sphaerospermum*, and *Agaricus biscporus* in comparison with *Sepia officinalis* and synthetic melanin.

To measure the optical absorption, ten milligrams of melanin powder isolated from each of the fungal sources were suspended in 1 mL of phosphate buffer solution and optical absorption was determined using a spectrometer. Sepia (M2649) and synthetic (M8631) melanin were purchased from Sigma-Aldrich for comparison. The isolated melanin from different melanotic fungal sources showed broadband optical absorption spectra (FIG. 10) typical of melanin.

Figure 11A:
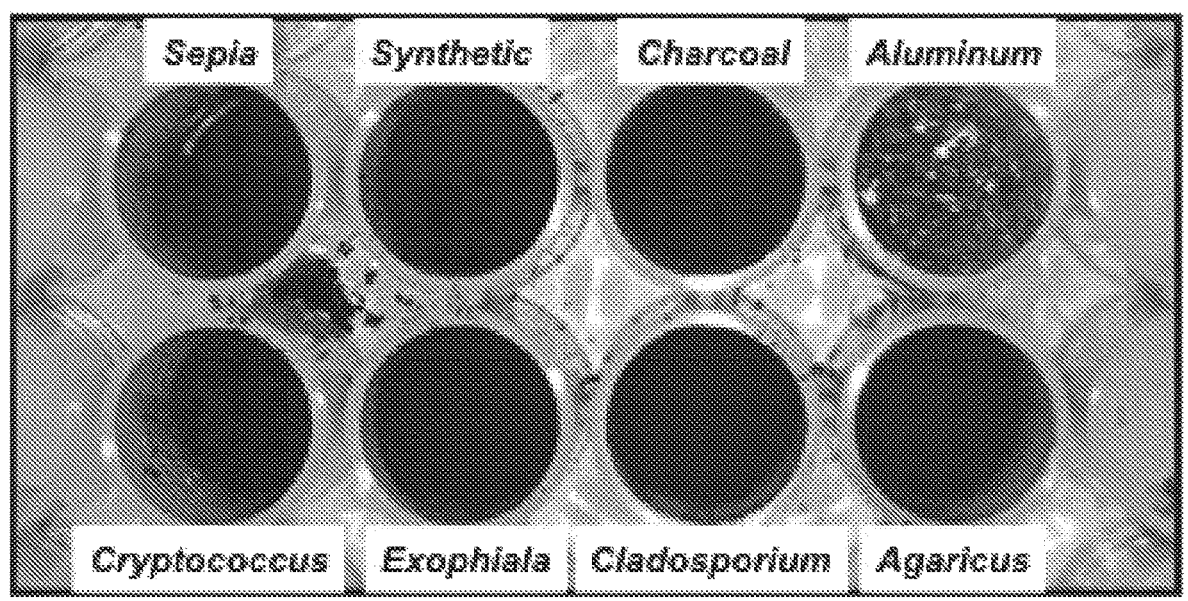
FIG. 11A and FIG. 11B show the heat capture by melanins isolated from various fungal sources.
Figure 11B:
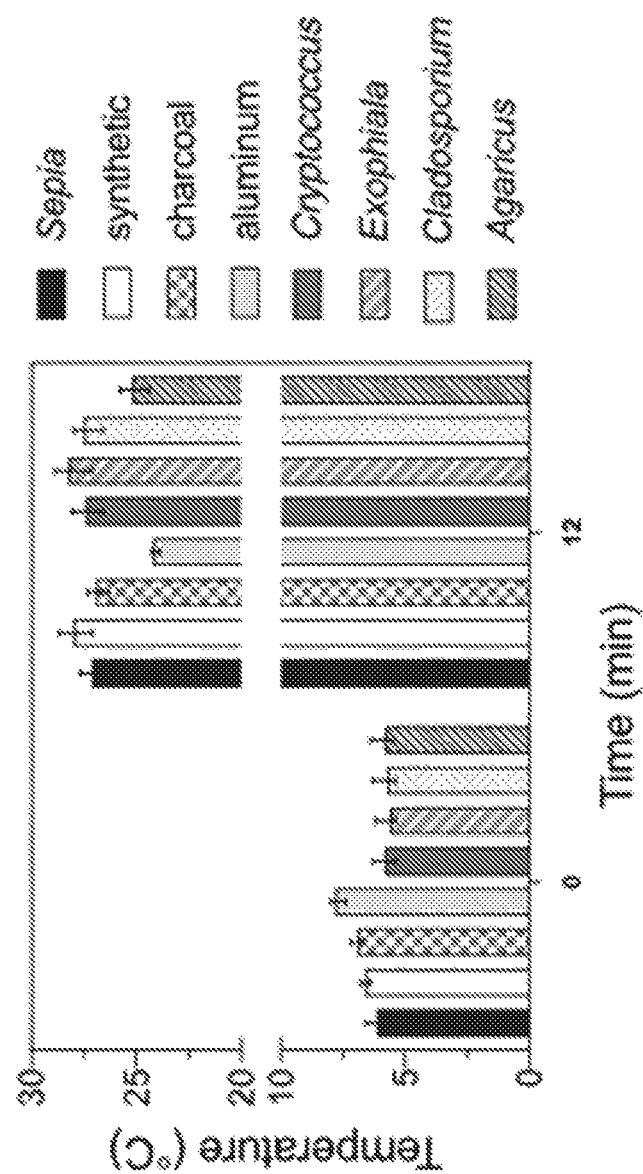
Figure 11B:
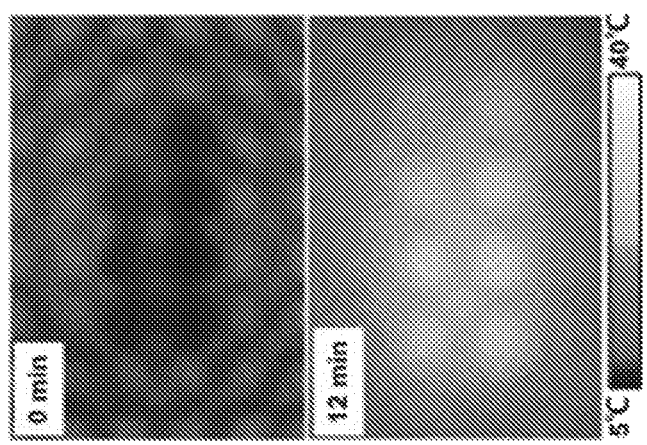

To measure the ability of the isolated melanins to capture heat from visible light, fifty milligrams of the isolated melanin powder was loaded in 48-well microtiter plates with equal masses of charcoal and aluminum foil for comparison. Samples were equilibrated at 4° C. before exposure to a white LED lamp for 12 mins. As shown in FIG. 11, all melanin powders increased in temperature following twelve minutes of radiation exposure.

Figure 12:
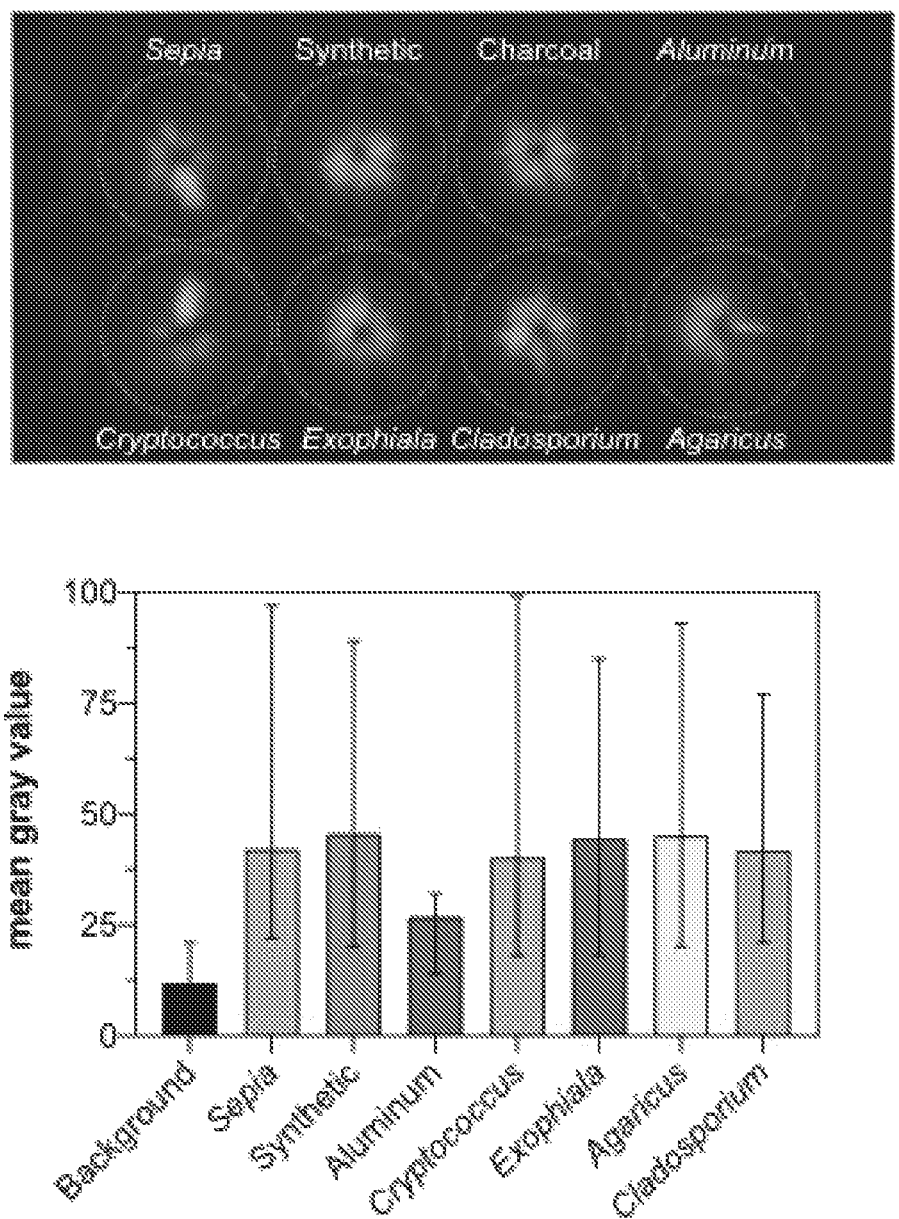
FIG. 12 shows that melanin isolated from different fungal sources can shield against ultraviolet radiation measured using radiography. The upper panel shows an image of the digital scan quantifying color intensity on shielded areas (light color means more shielding) The graph shows the quantification of color change as the mean gray value. Bars represent minimal and max modal values.

The ability of the isolated melanins to shield against ultraviolet radiation was also tested. The isolated melanin (50 mg) was placed on top of a radiography film and irradiated for 1 min with a ~280 nm UV lamp inside a Faraday box designed to control light intensity. Following irradiations, the film was developed and digitally scanned to quantify the change in color intensity on shielded areas. All the melanin powders also shielded against UV radiation (FIG. 12).

Example 8

Characterization of 3D Printed Objects

Figure 14A:
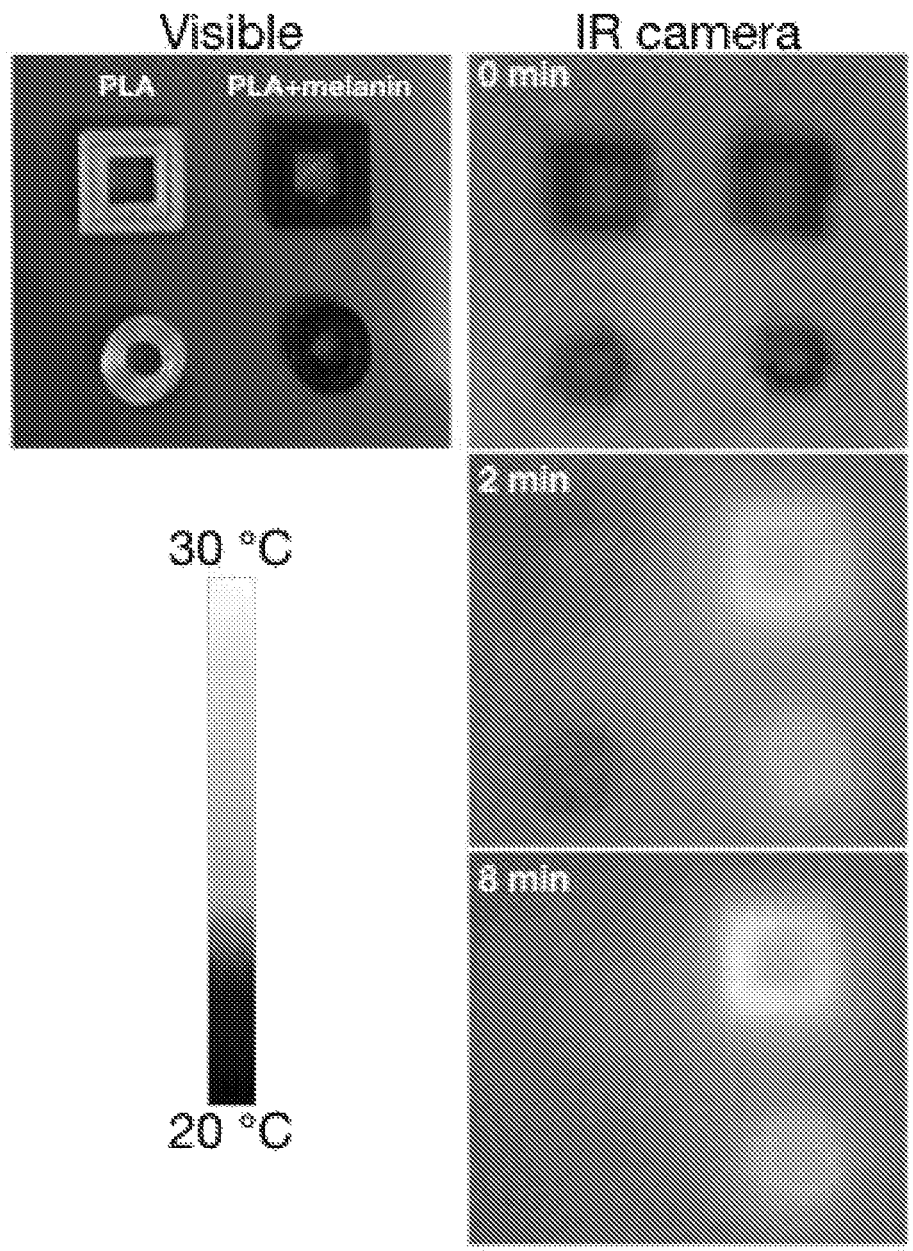
FIG. 14A and FIG. 14B show that 3D-printed objects using a melanin-PLA composite absorb heat from white LED light. Square (sq) and circle 3D objects were printed using a PLA+melanin (1%) composite, as shown in FIG. 12, and a commercial PLA filament.
Figure 14B:
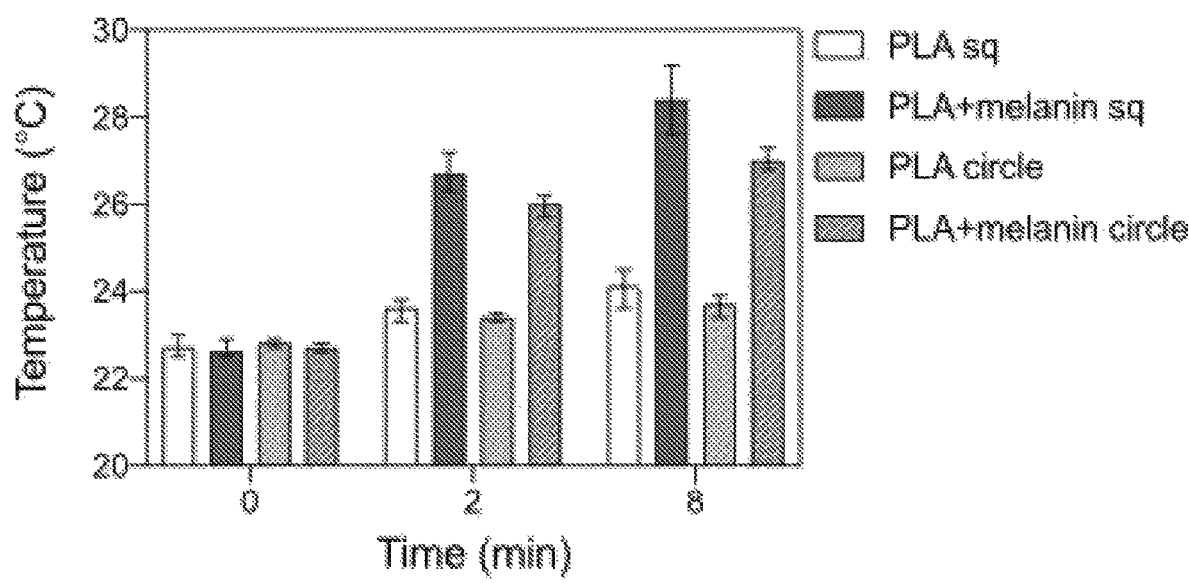

To measure the ability of the objects printed using the 3D-printable materials described in Example 6, two differently shaped articles were printed using the PLA+melanin composite and a commercial PLA filament (FIG. 14A, top left image). Thermal images (FIG. 14A, right column) were obtained before and following 2 and 8 minutes of exposure to a white LED lamp (LUX 75,000). As shown in FIG. 12, the presence of melanin increased the heat absorbing properties of PLA It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. An ultraviolet and visible light absorbing biocomposite comprising:
 a thermoplastic polymer, a thermoplastic elastomer, a metal, silicone, and combinations thereof, and
 melanin.

Clause 2. The biocomposite of clause 1, wherein the thermoplastic polymer, thermoplastic elastomer, metal, silicone, and combinations thereof are 3D printable materials.

Clause 3. The biocomposite of clause 1 or clause 2, wherein the thermoplastic polymer comprises acrylonitrile butadiene styrene (ABS), acrylic styrene acrylonitrile (ASA), nylon, polycarbonate, polyethylene terephthalate, polylactic acid (PLA), polypropylene or combinations thereof.

Clause 4. The biocomposite of any of clauses 1-3, wherein the thermoplastic polymer comprises polylactic acid.

Clause 5. The biocomposite of any of clauses 1-4, wherein the metal comprises aluminum, cobalt chrome, Inconel, stainless steel, titanium, tool steel, or combinations thereof.

Clause 6. The biocomposite of any of clauses 1-5, wherein the biocomposite comprises at least 1% by weight melanin.

Clause 7. The biocomposite of any of clauses 1-6, wherein the biocomposite comprises between 1% and 10% by weight melanin.

Clause 8. The biocomposite of any of clauses 1-7, wherein the melanin comprises melanin purified from biological sources, synthetic melanin, metal-complexed forms of melanin, or combinations thereof.

Clause 9. A method of purifying melanin for the biocomposite of clause 1 comprising the steps of:
 heating a melanin producing fungus in 6N hydrochloric acid (HCl); and
 extracting the melanin using a chloroform:methanol:saline mixture.

Clause 10. The method of clause 9, wherein the fungus is selected from the group consisting of *Cryptococcus neoformans, Aureobasidium melanogenum, Wingiella dermititidis, Cryomyces antarcticus* and *Cryptococcus* chs3, *Cryptococcus* csr2, *Cryptococcus* pgi1, modified cell wall mutants thereof, *Exophiala dermatitidis, Agaricus biseporus, Cladosporium sphaerospermum*, and combinations thereof.

Clause 11. The method of clause 9 or 10, wherein the heating step has a temperature in the range of 60° C. to 120° C.

Clause 12. The method of any of clauses 9-11, wherein the heating step has a duration in the range of 30 minutes to 24 hours.

Clause 13. The method of any of clauses 9-12, wherein the heating step has a duration of 30 minutes to 3 hours.

Clause 14. The method of any of clauses 9-13, wherein the mixture has a concentration of about 8 parts chloroform: 4 parts methanol; and 3 parts saline.

Clause 15. An article comprising the biocomposite of any of clauses 1-8.

Clause 16. A method of making an article of clause 15 comprising:
melting the thermoplastic polymer, thermoplastic elastomer, metal, silicone, and combinations thereof;
powdered melanin to the melted thermoplastic polymer, thermoplastic elastomer, metal, silicone, and combinations thereof, gradually with mixing to form a melted biocomposite material;
shaping the melted biocomposite material to form the article; and
cooling the article.

Clause 17. A method of making an article of clause 15 comprising:
combining a powder form of the thermoplastic polymer, thermoplastic elastomer, metal, silicone, and combinations thereof and powdered melanin to form a biocomposite powder;
dehydrating the biocomposite powder;
heating the biocomposite powder to create melted biocomposite material;
extruding the melted biocomposite material to form a filament for use in 3D printing;
melting the filament in a printing head of a 3D printer to form melted biocomposite; and
depositing melted biocomposite in successive layers to form the article.

Clause 18. A filament for 3D printing comprising:
a thermoplastic polymer, a thermoplastic elastomer, a metal, silicone, and combinations thereof; and
melanin.

Clause 19. The filament of clause 18, wherein the thermoplastic polymer comprises acrylonitrile butadiene styrene (ABS), acrylic styrene acrylonitrile (ASA), nylon, polycarbonate, polyethylene terephthalate, polylactic acid (PLA), polypropylene or combinations thereof.

Clause 20. The filament of clause 18 or clause 19, wherein the thermoplastic polymer comprises polylactic acid.

Clause 21. The filament of any one of clauses 18-20, wherein the metal comprises aluminum, cobalt chrome, Inconel, stainless steel, titanium, tool steel, or combinations thereof.

Clause 22. The filament of any of clauses 18-21, wherein the filament comprises at least 1% by weight melanin.

Clause 23. The filament of any of clauses 18-22, wherein the melanin comprises between 1% and 10% by weight melanin.

Clause 24. The filament of any of clauses 18-23, wherein the melanin comprises melanin purified from biological sources, synthetic melanin, metal-complexed forms of melanin, or combinations thereof.

Clause 25. A method of making the filament of any one of clauses 18-23 comprising:
combining a powder form of the thermoplastic polymer, thermoplastic elastomer, metal, silicone, and combinations thereof and powdered melanin to form a powder mixture;
dehydrating the powder mixture;
heating the powder mixture to create a melted powder mixture; and
extruding the melted powder mixture to form a filament for use in 3D printing;

Clause 26. A 3D printed item comprising:
a thermoplastic polymer, a thermoplastic elastomer, a metal, silicone, and combinations thereof; and
melanin.

Clause 27. A method of making the 3D printed item of clause 24 comprising:
melting the filament of any one of clauses 17-22 in a printing head of a 3D printer; and
depositing the melted filament material in successive layers to form the article.

Clause 28. Use of a filament comprising a thermoplastic polymer, a thermoplastic elastomer, a metal, silicone, and combinations thereof; and melanin in 3D printing.

What is claimed is:

1. An ultraviolet and visible light absorbing biocomposite mixture comprising: a thermoplastic polymer, a thermoplastic elastomer, a metal, silicone, and any combination thereof; and
melanin,
wherein: the thermoplastic polymer is acrylonitrile butadiene styrene (ABS), acrylic styrene acrylonitrile (ASA), nylon, polyethylene terephthalate, polylactic acid (PLA), polypropylene, or any combination thereof,
the metal comprises aluminum, cobalt chrome, Inconel, stainless steel, titanium, tool steel, or combinations thereof;
the biocomposite mixture comprises between 1% and 10% by weight melanin;
the melanin comprises melanin purified from biological sources, synthetic melanin, metal-complexed forms of melanin, or combinations thereof; and
the biocomposite mixture comprises at least 80% by weight of 3D printable materials.

2. The biocomposite mixture of claim 1, wherein the thermoplastic elastomer is styrenic block copolymers, thermoplastic polyurethanes, thermoplastic copolyester, or any combination thereof.

3. The biocomposite mixture of claim 1, wherein the thermoplastic polymer is polylactic acid (PLA).

4. The biocomposite mixture of claim 1, wherein the biocomposite mixture comprises polylactic acid and melanin.

5. The biocomposite mixture of claim 1, wherein the biocomposite mixture is malleable at or above room temperature.

6. The biocomposite mixture of claim 5, wherein the biocomposite mixture is solid at room temperature.

7. The biocomposite mixture of claim 5, wherein the biocomposite mixture is less malleable at room temperature than at above room temperature.

* * * * *